United States Patent [19]
Chisari et al.

[11] Patent Number: 5,840,303
[45] Date of Patent: Nov. 24, 1998

[54] PEPTIDES FOR INDUCING CYTOTOXIC T LYMPHOCYTE RESPONSES TO HEPATITIS B VIRUS

[75] Inventors: Francis V. Chisari, Del Mar, Calif.; Carlo Ferrari, Parma, Italy; Amalia Penna, Parma, Italy; Gabriele Missale, Parma, Italy

[73] Assignee: The Scripps Research Foundation, La Jolla, Calif.

[21] Appl. No.: 468,279

[22] Filed: Jun. 6, 1995

Related U.S. Application Data

[60] Division of Ser. No. 935,898, Aug. 26, 1992, abandoned, which is a continuation-in-part of Ser. No. 749,540, Aug. 26, 1991, abandoned.

[51] Int. Cl.$^6$ .......................... A61K 39/29; A61K 39/12; A61K 39/385; C07K 7/06
[52] U.S. Cl. ..................................... 424/189.1; 424/184.1; 424/185.1; 424/186.1; 424/193.1; 424/196.11; 424/204.1; 424/227.1; 514/2; 514/15; 530/300; 530/327; 530/328; 530/403
[58] Field of Search ............................. 424/184.1, 185.1, 424/186.1, 189.1, 193.1, 204.1, 225.1, 227.1, 278.1, 283.1, 450; 514/2, 13; 530/326, 327

[56] References Cited

U.S. PATENT DOCUMENTS

| | | | |
|---|---|---|---|
| 4,818,527 | 4/1989 | Thornton et al. | 424/88 |
| 5,100,662 | 3/1992 | Bolcsak et al. | 424/88 |

OTHER PUBLICATIONS

Bertoletti A; Sette A; Chisari F V; Penna A; Levrero M; De Carli M; Fiaccadori F; Ferrari C; "Natural variants of cytotoxic epitopes are T–cell receptor antagonists for antiviral cytotoxic T cells," Nature (2 Jun. 1994) 369: 407–410.

Ruppert, J; Sidney, J; Celis, E; Kubo, R T.; Grey, H M.; Sette, A, "Prominent role of secondary anchor residues in peptide binding to HLA–A2.1 molecules," Cell (1993), 74(5), 929–937.

Jameson S C; Carbone F R; Bevan M J, "Clone–specific T cell receptor antagonists of major histocompatibility complex class I–restricted cytotoxic T cells," Journal of Experimental Medicine, (1993 Jun 1) 177 (6) 1541–1550.

De Magistris M T; Alexander J; Coggeshall M; Altman A; Gaeta F C; Grey H M; Sette A, "Antigen analog–major histocompatibility complexes act as antagonists of the T cell receptor," Cell, (1992 Feb. 21) 68 (4) 625–634.

Vitiello A; Ishioka G; Grey H M; Rose R; Farness P; LaFond R; Yuan L; Chisari F V; Furze J; Bartholomeuz R; et al., "Development of a lipopeptide–based therapeutic vaccine to treat chronic HBV infection. I. Induction of a primary cytotoxic T lymphocyte response in humans," Journal of Clinical Investigation, (1995 Jan.) 95 (1) 341–349.

Hilleman, "Comparative Biology and Pathogenesis of AIDS and Hepatitis B Viruses: Related but Different", AIDS Res. Hum. Retrovir. 10, 1409–1419 (1994).

Bowie et al., "Deciphering the Message in Protein Sequences: Tolerance to Amino Acid Substitutions", Science 247, 1306–1310 (1990).

Kumar et al., "Amino acid variations at a single residue in an autoimmune peptide profoundly affect its properties:", Proc. Natl. Acad. Sci. USA 87, 1337–1341 (1990).

Carbone et al., "Induction of Cytotoxic T Cells by Primary in vitro Stimulation with Peptides", J. Exp. Med., 167, 1767–1779 (1988).

Lewin, "When Does Homolgy Mean Something Else?", Science 237, 1570 (1987).

Reeck et al., "Homology' in Proteins and Nucleic Acids: A Terminology Muddle and a Way out it", Cell 50, 667 (1987).

Falk et al., "Allele–specific motifs revealed by sequencing of self–peptides eluted from MHC molecules", Nature 351, 290–296 (May 1991).

Ferrari et al., "Identification of Immunodominant T Cell Epitopes of the Hepatitis B Virus Nucleocapsid Antigen", J. Clin. Invest. 88, 214–222 (Jul. 1991).

Deres et al., "In vivo priming of virus–specific cytotoxic T lymphocytes with synthetic lipopeptide vaccine", Nature 342, 561–564 (1989).

Galibert et al., "Nucleotide sequence of the hepatitis B virus genome (subtype ayw)cloned in E. coli", Nature 281, 646–650 (1979).

Bichko et al., "Subtype ayw variant of hepatitis B virus", FEBS Lett. 185, 208–212 (1985).

Mack et al., "Hepatitis B Virus Particles Contain a Polypeptide Encoded by the Largest Open Reading Frame: A Putative Reverse Transcriptase", J. Virol. 62, 4786–4790 (1988).

*Primary Examiner*—Michael P. Woodward
*Attorney, Agent, or Firm*—Townsend and Townsend and Crew

[57] ABSTRACT

Peptides are used to define epitopes that stimulate HLA-restricted cytotoxic T lymphocyte activity against hepatitis B virus antigens. The peptides are derived from regions of HBV nucleocapsid, envelope, polymerase and the transcriptional transactivator X protein, and are particularly useful in treating or preventing HBV infection, including methods for stimulating the immune response of chronically infected individuals to respond to HBV antigens. Pharmaceutical compositions and hepatitis B vaccines which comprise the peptides and physiologically acceptable carriers can be employed in conjunction with other HBV vaccines to provide more effective immunity against the disease. Methods for identifying individuals who are particularly susceptible to developing chronic HBV infection and who can be targeted for treatment by the CTL peptides are also provided.

12 Claims, 17 Drawing Sheets

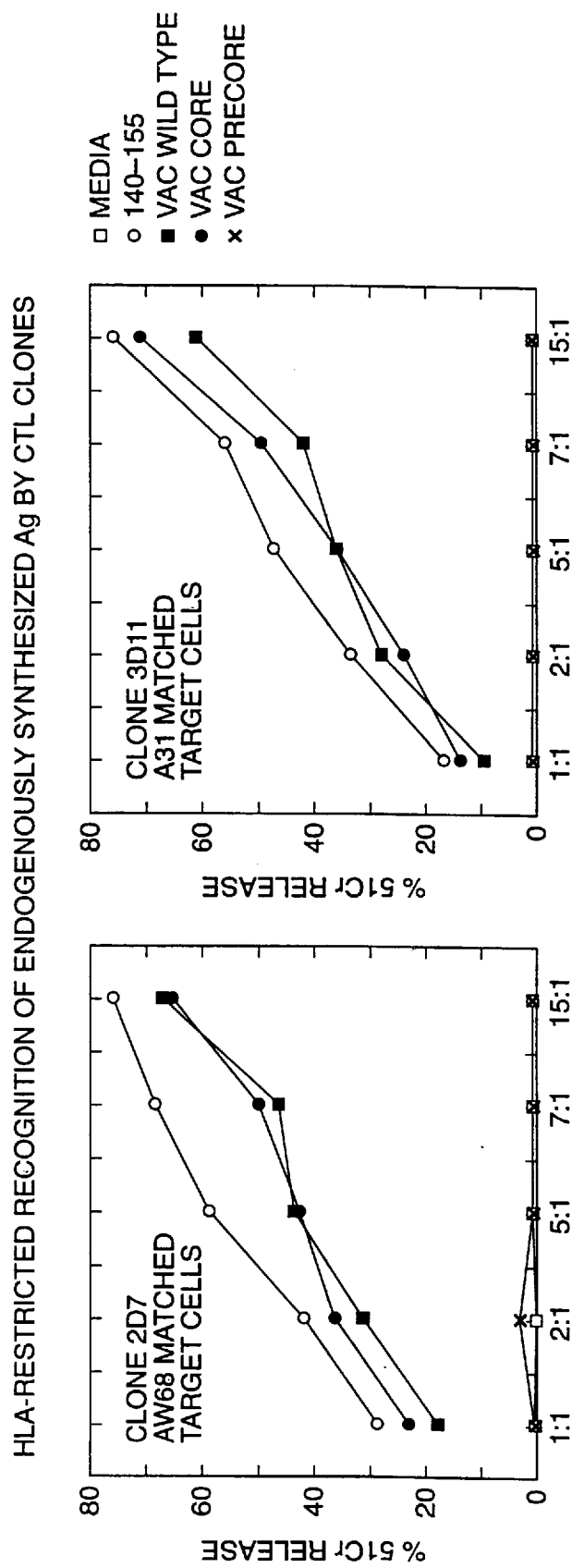

PEPTIDES FOR INDUCING CYTOTOXIC T LYMPHOCYTE RESPONSES TO HEPATITIS B VIRUS

RELATED APPLICATIONS

This application is a divisional of Ser. No. 07/935,898, filed Aug. 26, 1992, now abandoned, which is a continuation-in-part of Ser. No. 07/749,540, filed Aug. 26, 1991, now abandoned, each of which are incorporated herein by reference.

GOVERNMENT SUPPORT

The U.S. Government may have certain rights in this invention pursuant to grants awarded by the National Institutes of Health.

BACKGROUND OF THE INVENTION

The hepatitis B virus (HBV) infects hepatocytes and causes acute and chronic liver disease and hepatocellular carcinoma. Infection is typically via contaminated blood or body fluids, and thus HBV infection is prevalent among intravenous drug abusers, homosexuals, and in countries with less developed health care systems where the risk of exposure to contaminated blood products is high. Approximately 90–95% of infected individuals are able to resolve their infection, while the remaining 5–10% develop chronic hepatitis and lapse into a carrier state, with the possibility of later developing liver cirrhosis and/or hepatocellular carcinoma. It has recently been estimated that throughout the world there are approximately 250 million people who are chronic carriers of HBV.

The pathogenic mechanisms responsible for liver cell injury in HBV infection are not well understood, although it is believed that the virus is not directly cytopathic. Since HBV does not readily infect human cells in vitro, however, the virus has been extremely difficult to study. Consequently, as yet there is no effective treatment for an established HBV infection.

It is widely believed that HBsAg is the HBV antigen that induces a protective immune response which allows most infected individuals to resolve their infection via protective antibody. In fact, anti-HBV envelope antibodies can neutralize HBV particles, and thus vaccines have been developed based on HBsAg that prevent HBV infection from becoming established. The vaccines employ HBsAg purified from the plasma of chronic HBV carriers, or HBsAg produced by recombinant DNA technology. Synthetic HBsAg peptide-based vaccines have also been proposed. See, for example, U.S. Pat. Nos. 4,599,230 and 4,599,231. The anti-HBsAg vaccines, however, afford protection in only about 90% of immunized individuals. Those who are immunized but unprotected provide a significant and unsuspecting reservoir of potential infection.

The role of the HBV nucleocapsid core antigen (HBcAg) in developing a protective immunity is less clear. In some instances, immunization of chimpanzees and woodchucks with nucleocapsid core antigen (HBcAg or WHcAg) has provided complete or partial protection against HBV and WHV infection. HBcAg-specific helper T cells have also be shown to support anti-envelope antibody production by HBV envelope-specific B cells. HBcAg has also been reported as a sensitizing antigen for intrahepatic T cells during chronic HBV infection.

The contribution of other forms of immunity to HBV antigens, particularly that involving cytotoxic T lymphocytes, has also been difficult to assess. Chisari et al. (*Microbial pathogen.* 6:31 (1989)) have suggested that liver cell injury may be mediated by an HLA-Class I restricted, $CD8^+$ cytotoxic T cell response to HBV encoded antigen. Class I major histocompatibility (MHC)-restricted cytotoxic T lymphocyte responses have been identified for a variety of other viruses, such as influenza. For example, Townsend et al., *Cell* 44:959 (1986) reported that epitopes of an influenza virus nucleoprotein recognized by cytotoxic T lymphocytes could be defined by synthetic peptides. In attempting to define the cytotoxic T lymphocyte response to HBV, it has been shown that peripheral blood lymphocytes from patients with acute and chronic HBV may be able to kill autologous hepatocytes in vitro, but the specificity of the cytolytic activity, its HLA restriction elements, and cellular phenotype were not established. See, Mondelli et al., *J. Immunol.* 129:2773 (1982) and Mondelli et al., *Clin. Exp. Immunol.* 6:311 (1987). More recently, Moriyama et al., Science 248:361–364 (1990), reported that the HBV major envelope antigen was expressed at the hepatocyte surface in a form recognizable by MHC class I-restricted, $CD8^+$ cytotoxic T lymphocytes, and by envelope-specific antibodies.

Although different strains of HBV exist, they each share at least one common envelope determinant, which is designated "a". Each strain also has two other envelope determinants, one of which is either "d" or "y", and the second is either "w" or "r". Thus, there are four possible subtypes of the virus: adw, ayw, adr, and ayr. The cloning, sequencing and expression of HBV are described in GB 2034323, EP 13828, U.S. Pat. No. 4,935,235, and the complete sequence of the HBV nucleocapsid region is also described in Galibert et al., *Nature* 281:646 (1979), each of the foregoing being incorporated herein by reference.

As the presently approved HBV vaccines provide only about 90% protection among immunized individuals, it would be desirable to elicit more effective immunity, such as by increasing or diversifying the immunogenicity of the vaccines. It would also be desirable to stimulate the immune responses of individuals chronically infected with HBV to respond to appropriate HBV antigens and eliminate the infection, or to prevent the evolution from an acute to a chronic infection. Further, means for predicting which patients acutely infected with HBV are likely to develop chronic infection as HBV carriers would allow appropriate treatment and/or precautions to be implemented early in the infectious process. Quite surprisingly, the present invention fulfills these and other related needs.

SUMMARY OF THE INVENTION

The present invention provides peptides which induce MHC class I restricted cytotoxic T lymphocyte responses against HBV antigen. The peptides of interest are derived from the HBV nucleocapsid. In certain embodiments the peptides comprise from six to about fifty amino acids and have at least four contiguous amino acids from within the sequence II ($HBc_{19-27}$) [Seq. ID No. 4]Leu-Pro-Ser-Asp-Phe-Phe-Pro-Ser-Val, wherein the peptide can be optionally flanked and/or modified at one or both of the N- and C-termini, as desired. In preferred embodiments the peptide sequence are Ala-Thr-Val-Glu-Leu-Leu-Ser-Phe-Leu-Pro-Ser-Asp-Phe-Phe-Pro-Ser-Val, ($HBc_{11-27}$) [Seq. ID No. 2], and Leu-Pro-Ser-Asp-Phe-Phe-Pro-Ser-Val ($HBc_{19-27}$) [Seq. ID No. 4], which regions are conserved among the major subtypes of HBV, although substitutions, deletions and additions may be made to the peptide without substantially adversely affecting its biological activity.

In other embodiments the peptides are from six to about fifty amino acids and have at least four contiguous residues from the sequence V (HBc$_{140-154}$) [Seq. ID No. 7]Leu-Ser-Thr-Leu-Pro-Glu-Thr-Thr-Val-VAl-Arg-Arg-Arg-Gly-Arg, wherein the peptide can be optionally flanked and/or modified at one or both of the N- and C-termini, as desired. In other embodiments the peptides are derived from at least seven contiguous amino acids of the sequence of HBc$_{111-125}$, wherein HBc$_{111-125}$ for HBV subtype awy has the sequence Gly-Arg-Glu-Thr-Val-Ile-Glu-Tyr-Leu-Val-Ser-Phe-Gly-Val-Trp [Seq. ID No. 6], wherein termini may be also modified as mentioned above. For the HBV subtype adw, the Ile$_{116}$ is replaced by Leu. In yet another embodiment a peptide which induces a MHC class I-restricted cytotoxic T lymphocyte response is peptide VI (HBc$_{28-47}$) [Seq. ID No. 8] having the sequence Arg-Asp-Leu-Leu-Asp-Thr-Ala-Ser-Ala-Leu-Tyr-Arg-Glu-Ala-Leu-Glu-Ser-Pro-Glu-His, wherein termini of the selected peptide can also be modified, as desired.

In the various peptide embodiments it will be understood that the peptides can be polymerized, each to itself to form larger homopolymers, or with different peptides to form heteropolymers. In some instances peptides will be combined in a composition as an admixture and will not be linked. The peptide can also be conjugated to a lipid-containing molecule capable of enhancing a T lymphocyte response, or to a different peptide which induces a T-helper cell response, for example.

Compositions are provided which comprise a peptide of the invention formulated with an additional peptide, a liposome, an adjuvant and/or a pharmaceutically acceptable carrier. Thus, pharmaceutical compositions can be used in methods of treating acute HBV infection, particularly in an effort to prevent the infection from progressing to a chronic or carrier state. Methods for treating chronic HBV infection and HBV carrier states are also provided, where the pharmaceutical compositions are administered to infected individuals in amounts sufficient to stimulate immunogenically effective cytotoxic T cell responses against HBc epitopes. For treating these infections it may be particularly desirable to combine the peptides which induce MHC class I restricted cytotoxic T lymphocyte responses against HBV antigen with other peptides or proteins that induce immune response to other HBV antigens, such as HBsAg. To treat individuals with chronic or carrier state infections the compositions may be administered in repeated dosages over a prolonged period of time, as necessary, to resolve or substantially mitigate the infection and/or shedding of virus.

Vaccine compositions for preventing HBV infection, particularly chronic HBV infection, are also provided. The vaccine compositions comprise an immunogenically effective amount of a HBV nucleocapsid peptide which induces a MHC class I restricted cytotoxic T lymphocyte response, such as HBcAg$_{11-27}$ of the sequence Ala-Thr-Val-Glu-Leu-Leu-Ser-Phe-Leu-Pro-Ser-Asp-Phe-Phe-Pro-Ser-Val, particularly in the case of HLA-A2 haplotype individuals, and will typically further comprise an adjuvant, e.g., incomplete Freund's adjuvant or aluminum hydroxide. To achieve enhanced protection against HBV, the vaccine can further comprise components which elicit a protective antibody response to HBV envelope antigen.

In yet other embodiments the invention relates to methods for diagnosis, where the peptides of the invention are used to determine the presence of lymphocytes in an individual which are capable of a cytotoxic T cell response to HBV nucleocapsid antigen. The absence of such cells determines whether the individual of interest is susceptible to developing chronic HBV infection. Typically the lymphocytes are peripheral blood lymphocytes and the individual of interest is suffering from an acute HBV infection.

BRIEF DESCRIPTION OF THE DRAWINGS

FIG. 2 illustrates the cytotoxic T cell activity observed with the peptide pools in each of patients M. B.

FIGS. 11A–11B illustrates that CTL clones 2D7 and 3D11 can lyse target cells expressing the endogenously synthesized antigen in a HLA-restricted manner. Clones 2D7 and 3D11 were tested against allogeneic target cells respectively Aw68 and A31 positive preincubated with peptide 140–155, and infected with recombinant vaccinia viruses coding for the core and precore protein of HBV.

DESCRIPTION OF THE SPECIFIC EMBODIMENTS

Figure 1:
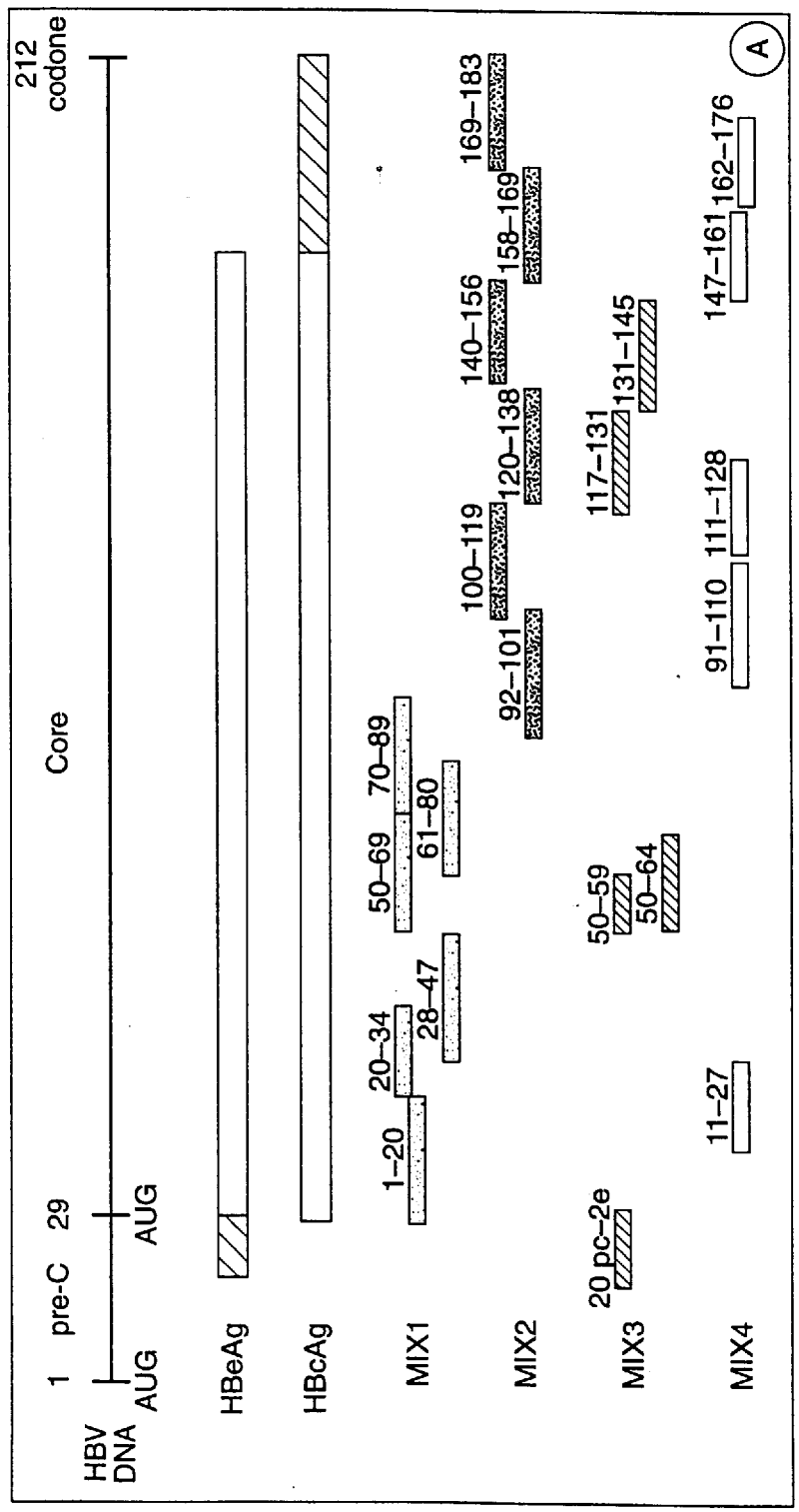
FIG. 1 shows the peptides used in pools to stimulate peripheral blood mononuclear cells to identify HBV-specific cytotoxic T lymphocytes.

The present invention provides peptides derived from HBV proteins for use in compositions and methods for the treatment, prevention and diagnosis of HBV infection. The peptides stimulate MHC HLA-class I restricted cytotoxic T lymphocyte responses to HBV infected cells. The stimulated cytotoxic T lymphocytes are able to kill the infected cells or inhibit viral replication and thus interrupt or substantially prevent infection, including chronic HBV infection. A peptide effective in eliciting a cytotoxic T cell response may also be combined with an immunogen capable of eliciting a T-helper response.

In one aspect the peptides employed in the invention are derived from within two independent HBV nucleocapsid (HBc) polypeptides, core and precore. Precore contains an amino-terminal signal sequence that leads to its translocation into the endoplasmic reticulum and secretion as HBeA, while core is primarily a cytoplasmic and nuclear protein (HBcAg) and is not secreted. The peptides are derived from the region of HBc residues 19–27, HBc$_{28-47}$, HBc$_{111-125}$, HBc$_{140-154}$ (particularly HBc$_{141-151}$), where the numbering is according to Galibert et al., supra. In other embodiments the peptides are from the sequence of the HBV polymerase protein (HBpol), particularly CTL epitopes within HBpol$_{61-69}$ and HBpol$_{803-811}$. In yet other embodiments the peptides contain CTL-inducing epitopes derived from the HBV transcriptional transactivator protein, HBx, and more particularly from the region of HBx$_{126-134}$. The CTL-inducing peptides can also be prepared from the HB envelope antigen, particularly the peptide which corresponds to the HBV sequence of HBenv$_{348-357}$.

By HBV cytotoxic T lymphocyte inducing "peptide" or "oligopeptide" of the present invention is meant a chain of at least four HBV amino acid sequence residues, preferably at least six, more preferably eight or nine, sometimes ten to twelve residues, and usually fewer than about fifty residues, more usually fewer than about thirty-five, and preferably fewer than twenty-five, e.g., eight to seventeen amino acid residues derived from an HBc sequence. It may be desirable to optimize peptides of the invention to a length of eight to twelve amino acid residues, commensurate in size with endogenously processed viral peptides that are bound to MHC class I molecules on the cell surface. See generally, Schumacher et al., Nature 350:703–706 (1991); Van Bleek et al., Nature 348:213–216 (1990); Rotzschke et al., Nature 348:252–254 (1990); and Falk et al., Nature 351:290–296 (1991), which are incorporated herein by reference. As set forth in more detail below, usually the peptides will have at least a majority of amino acids which are homologous to a corresponding portion of contiguous residues of the HBV sequences identified herein, and containing a CTL-inducing epitope.

The peptides can be prepared "synthetically," as described hereinbelow, or by recombinant DNA technology. Although the peptide will preferably be substantially free of other naturally occurring HBV proteins and fragments thereof, in some embodiments the peptides can be synthetically conjugated to native fragments or particles. The term peptide is used interchangeably with polypeptide in the present specification to designate a series of amino acids connected one to the other by peptide bonds between the alpha-amino and alpha-carboxy groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

Desirably, the peptide will be as small as possible while still maintaining substantially all of the biological activity of the large peptide. By biological activity is meant the ability to bind an appropriate MHC molecule and induce a cytotoxic T lymphocyte response against HBV antigen or antigen mimetic. By a cytotoxic T lymphocyte response is meant a CD8$^+$ T lymphocyte response specific for an HBV antigen of interest, wherein CD8$^+$, MHC class I-restricted T lymphocytes are activated. The activated T lymphocytes secrete lymphokines (e.g., gamma interferon) liberate products (e.g., serine esterases) that inhibit viral replication in infected autologous cells or transfected cells, with or without cell killing.

The terms "homologous", "substantially homologous", and "substantial homology" as used herein denote a sequence of amino acids having at least 50% identity wherein one sequence is compared to a reference sequence of amino acids. The percentage of sequence identity or homology is calculated by comparing one to another when aligned to corresponding portions of the reference sequence.

A CTL-inducing HBV peptide embodiment of the invention from the nucleocapsid region comprises from six to thirty-five amino acids and contains at least one HLA-restricted CTL epitopic site from the peptide region $HBc_{11-27}$. A majority of the amino acids of the peptide will be identical or substantially homologous to the amino acids of the corresponding portions of the naturally occurring $HBc_{11-27}$ region, where $HBc_{11-27}$ has the sequence:

I ($HBc_{11-27}$) Ala-Thr-Val-Glu-Leu-Leu-Ser-Phe-Leu-Pro-Ser-Asp-Phe-Phe-Pro-Ser-Val.

The peptide embodiments of this $HBc_{11-27}$ region can be optionally flanked and/or modified at one or both of the N- and C-termini, as desired, by amino acids from HBV sequences, including HBc, amino acids added to facilitate linking, other N- and C-terminal modifications, linked to carriers, etc., as further described herein. The peptide $HBc_{11-27}$ induces a cytotoxic T lymphocyte response which is mediated by at least the MHC class I molecule HLA-A2.

Within the peptide I region are peptides which comprise the 9-mer peptide $HBc_{19-27}$ and contain a HLA-restricted CTL-inducing epitope, and peptides derived therefrom which contain a CTL-inducing epitopic site(s) of at least four contiguous amino acids of the sequence of $HBc_{19-27}$, wherein $HBc_{19-27}$ has the following sequence:

II ($HBc_{19-27}$) [Seq. ID No. 4]Leu-Pro-Ser-Asp-Phe-Phe-Pro-Ser-Val, wherein the peptide can be flanked and/or modified at one or both termini as mentioned for peptide I above. As with peptide I, peptide II induces a cytotoxic T lymphocyte response which is mediated by at least HLA-A2.

A particularly preferred peptide embodiment in the peptide I/II region is a 10-mer, $HBc_{18-27}$, which has the following sequence:

III ($HBc_{18-27}$) [Seq. ID No. 5]Phe-Leu-Pro-Ser-Asp-Phe-Phe-Pro-Ser-Val, wherein the peptide can be modified and/or flanked as previously mentioned.

Another HBc peptide embodiment of the invention comprises the 15-mer peptide $HBc_{111-125}$, and peptides derived from $HBc_{111-125}$ which contain a CTL-inducing HLA class I-restricted epitopic site(s) of at least seven contiguous amino acids. A majority of the amino acids of the peptide will be identical or substantially homologous to the amino acids of the corresponding portions of the naturally occurring $HBc_{111-125}$ sequence, where $HBc_{111-125}$ has the sequence (for HBV subtype ayw):

IV ($HBc_{111-125}$) [Seq. ID No. 6]Gly-Arg-Glu-Thr-Val-Ile-Glu-Tyr-Leu-Val-Ser-Phe-Gly-Val-Trp.

The peptide from the $HBc_{111-125}$ region can be flanked and/or modified at one or both termini as described herein. In a peptide of the HBV subtype adw, $Ile_{116}$ is replaced by Leu.

In another embodiment, a peptide of the invention comprises the 15-mer peptide $HBc_{140-154}$, and peptides derived from $HBc_{140-154}$ which contain a CTL-inducing HLA class I-restricted epitopic site(s) of at least ten contiguous amino acids. A majority of the amino acids of the peptide will be identical or substantially homologous to the amino acids of the corresponding portions of the naturally occurring $HBc_{140-154}$ sequence, where $HBc_{140-154}$ has the sequence (for HBV subtype ayw):

V ($HBc_{140-154}$) [Seq. ID No. 7]Leu-Ser-Thr-Leu-Pro-Glu-Thr-Thr-Val-Val-Arg-Arg-Arg-Gly-Arg

A peptide prepared from this region can be flanked and/or modified at one or both termini as described herein. The peptide V ($HBc_{140-154}$) induces a cytotoxic T lymphocyte response which is mediated by at least one MHC class I molecule, HLA-A31, and can also be restricted by HLA-Aw68. As shown in more detail in the Example section below, the sequence of $HBcl_{141-151}$ contains the minimal, optimally recognized epitope for both the A31 and Aw68 restriction elements.

Yet other CTL-inducing peptides of the invention are from the region of $HBc_{28-47}$, and includes peptides derived from $HBc_{28-47}$ which contain one or more CTL-inducing HLA class I-restricted epitopic site(s) of at least seven contiguous amino acids. A majority of the amino acids of the peptide will be identical or substantially homologous to the amino acids of the corresponding portions of the naturally occurring $HBc_{28-47}$ sequence, where $HBc_{28-47}$ has the sequence (for HBV subtype ayw):

VI ($HBc_{28-47}$) [Seq. ID No. 8]Arg-Asp-Leu-Leu-Asp-Thr-Ala-Ser-Ala-Leu-Tyr-Arg-Glu-Ala-Leu-Glu-Ser-Pro-Glu-His, wherein the selected peptide can be flanked and/or modified at one or both termini as described herein.

In other embodiments of the present invention, the peptides of the invention contain CTL-inducing epitopes derived from the polymerase protein. More particularly, the peptides are from the region of $HBpol_{61-69}$ or $HBpol_{803-811}$, and include peptides derived from those sequence regions which contain one or more CTL-inducing HLA class I-restricted epitopic site(s) of at least seven contiguous amino acids. A majority of the amino acids of the peptide will be identical or substantially homologous to the amino acids of the corresponding portions of the naturally occurring $HBpol_{61-69}$ or $HBpol_{803-811}$ sequences, where $HBpol_{61-69}$ and $HBpol_{803-811}$ have the following sequences (for HBV subtype ayw):

VII ($HBpol_{61-69}$) [Seq. ID No. 9]Gly-Leu-Tyr-Ser-Ser-Thr-Val-Pro-Val, and

VIII ($HBpol_{803-811}$) [Seq. ID No. 10]Ser-Leu-Tyr-Ala-Asp-Ser-Pro-Ser-Val, wherein the selected peptide can be flanked and/or modified at one or both termini as described herein.

Peptides of the present invention which contain anti-HBV CTL-inducing epitopes are also derived from the HBV transcriptional activator protein X. Although a variety of HBx peptides having CTL including activity can be identified as described herein, preferably, the peptides are from the region of $HBx_{126-134}$. Peptides derived from this sequence region contain one or more CTL-inducing HLA class I-restricted epitopic site(s) of at least seven contiguous amino acids. A majority of the amino acids of the peptide prepared from this region will be identical or substantially homologous to the amino acids of the corresponding portions of the naturally occurring $HBx_{126-134}$ sequence, where $HBx_{126-134}$ has the following sequence:

IX ($HBx_{126-134}$) [Seq. ID No. 3]Glu-Ile-Arg-Leu-Lys-Val-Phe-Val-Leu, wherein the peptide prepared from this region can be flanked and/or modified at one or both termini as described herein.

CTL-inducing peptides are also derived from the HBV envelope protein, and more particularly, the peptide is HBenv348–357 and is HLA class I-restricted, where $HBenv_{348-357}$ has the following sequence (for subtype ayw):

X ($HBenv_{348-357}$) [Seq. ID No. 11]Gly-Leu-Ser-Pro-Thr-Val-Trp-Leu-Ser-Val, wherein the peptide prepared from this region can be flanked and/or modified at one or both termini as described herein. The sequence for the adw subtype of HBenv348–357 has an alanine substituted for valine at the carboxy terminal residue.

As mentioned above, additional amino acids can be added to the termini of an oligopeptide or peptide to provide for ease of linking peptides one to another, for coupling to a carrier, support or a larger peptide, for reasons discussed herein, or for modifying the physical or chemical properties of the peptide or oligopeptide, and the like. Amino acids such as tyrosine, cysteine, lysine, glutamic or aspartic acid, and the like, can be introduced at the C- or N-terminus of the peptide or oligopeptide. In addition, the peptide or oligopeptide sequences can differ from the natural sequence by being modified by terminal-$NH_2$ acylation, e.g., acetylation, or thioglycolic acid amidation, terminal-carboxy amidation, e.g., ammonia, methylamine, etc. In some instances these modifications may provide sites for linking to a support or other molecule.

It will be understood that the HBV peptides of the present invention or analogs thereof which have cytotoxic T lymphocyte stimulating activity may be modified as necessary to provide certain other desired attributes, e.g., improved pharmacological characteristics, while increasing or at least retaining substantially the biological activity of the unmodified peptide. For instance, the peptides can be modified by extending, decreasing or substituting amino acids in the peptide sequence by, e.g., the addition or deletion of amino acids on either the amino terminal or carboxy terminal end, or both, of peptides derived from the sequences disclosed herein. The peptides may be modified to substantially enhance the CTL inducing activity, such that the modified peptide analogs have CTL activity greater than a peptide of the wild-type sequence. For example, it may be desirable to increase the hydrophobicity of the N-terminal of a peptide, particularly where the second residue of the N-terminal is hydrophobic and is implicated in binding to the HLA restriction molecule. By increasing hydrophobicity at the N-terminal, the efficiency of the presentation to T cells may be increased. For example, as described below in the Experimental section, the wild type $HBx_{126-134}$ peptide has little CTL activity; but, by substituting the amino terminus Glu, a relatively polar and positively charged residue, with Ala, a nonpolar hydrophobic molecule, the CTL inducing activity was significantly enhanced. Peptides prepared from other disease associated antigens, particularly those containing CTL inducing epitopes for which a host may not have significant CTL activity, may be made CTL-inducing by substituting hydrophobic residues at the N-terminus of the peptide where the second residue is normally hydrophobic.

The peptides employed in the subject invention need not be identical to peptides I-X, or to a particular HBV nucleocapsid, envelope, polymerase or X protein sequence, so long as the subject compounds are able to provide for cytotoxic T lymphocytic activity against at least one of the four major subtypes of HBV. Therefore, the peptides may be subject to various changes, such as insertions, deletions, and substitutions, either conservative or non-conservative, where such changes provide for certain advantages in their use. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Usually, the portion of the sequence which is intended to substantially mimic an HBV cytotoxic T lymphocyte stimulating epitope will not differ by more than about 20% from the sequence of at least one subtype of HBV, except where additional amino acids may be added at either terminus for the purpose of modifying the physical or chemical properties of the peptide for, e.g., ease of linking or coupling, and the like. Where regions of the peptide sequences are found to be polymorphic among HBV subtypes, it may be desirable to vary one or more particular amino acids to more effectively mimic differing cytotoxic T-lymphocyte epitopes of different HBV strains or subtypes.

Within the peptide sequences identified by the present invention, including the representative peptide I ($HBc_{11-27}$), peptide II ($HBc_{19-27}$), peptide III ($HBc_{18-27}$), peptide IV ($HBc_{111125}$), peptide V ($HBc_{140-154}$), peptide VI ($HBc_{28-47}$), peptide VII ($HBpol_{61-69}$), peptide VIII ($HBpol_{803-811}$), and peptide IX ($HBx_{126-134}$), there are residues (or those which are substantially functionally equivalent) which allow the peptide to retain their biological activity, i.e., the ability to stimulate a class I-restricted cytotoxic T-lymphocytic response against HBV infected cells or cells which express HBV antigen. These residues can be identified by single amino acid substitutions, deletions, or insertions. In addition, the contributions made by the side chains of the residues can be probed via a systematic scan with a specified amino acid (e.g., Ala). Peptides which tolerate multiple substitutions generally incorporate such substitutions as small, relatively neutral molecules, e.g., Ala, Gly, Pro, or similar residues. The number and types of residues which can be substituted, added or subtracted will depend on the spacing necessary between the essential epitopic points and certain conformational and functional attributes which are sought (e.g., hydrophobicity vs. hydrophilicity). If desired, increased binding affinity of peptide analogues to its MHC molecule for presentation to a cytotoxic T-lymphocyte can also be achieved by such alterations, as exemplified by the $HBx_{126-134}$ peptide mentioned above. Generally, any spacer substitutions, additions or deletions between epitopic and/or conformationally important residues will employ amino acids or moieties chosen to avoid steric and charge interference which might disrupt binding.

Peptides which tolerate multiple substitutions while retaining the desired biological activity may also be synthesized as D-amino acid containing peptides. Such peptides may be synthesized as "inverso" or "retro-inverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions may more than compensate for a difference in affinity compared to the corresponding L-peptide. Further, L-amino acid-containing peptides with or without substitutions can be capped with a D-amino acid to inhibit exopeptidase destruction of the antigenic peptide.

In addition to the exemplary peptides described herein, the invention provides methods for identifying other epitopic regions associated with inducing MHC-restricted cytotoxic T lymphocyte responses against HBV or other viruses, such as HCV, HIV etc. The methods comprise obtaining peripheral blood lymphocytes (PBL) from infected or uninfected individuals and exposing (stimulating) the cells with synthetic peptide or polypeptide fragments derived from a protein of the pathogen or antigen of interest. In instances where the amino acid sequence of the protein(s) or antigen is known, pools of overlapping synthetic peptides, each typically about 8 to 20 residues long, can be used to stimulate the cells. Active peptides can be selected from pools which induce cytotoxic T lymphocyte activity. The ability of the peptides to induce specific cytotoxic activity is determined by incubating the stimulated PBL with autologous labeled (e.g., $^{51}Cr$) target cells (such as HLA matched macrophages, T cells, fibroblasts or B lymphoblastoid cells) infected or transfected with the pathogen or subgenomic fragments thereof, such that the targeted antigen is synthesized endogenously by the cell (or the cell is pulsed with the peptide of interest), and measuring specific release of label.

Once a peptide having an epitopic region which stimulates a cytotoxic T lymphocyte response is identified, the MHC restriction element of the response can be determined. This involves incubating the stimulated PBL or short term lines thereof with a panel of (labeled) target cells of known HLA types which have been pulsed with the peptide of interest, or appropriate controls. The HLA allele(s) of cells in the panel which are lysed by the CTL are compared to cells not lysed, and the HLA restriction element(s) for the cytotoxic T lymphocyte response to the antigen of interest is identified.

Carbone et al., *J. Exp. Med*, 167:1767 (1988), have reported that stimulation with peptides may induce cytotoxic T lymphocytes with low affinity for corresponding endogenous protein, such that repetitive peptide stimulation may yield cytotoxic T lymphocytes that recognize peptide but not native antigen. As the inability of stimulated cytotoxic T lymphocytes to recognize native HBV proteins would be undesirable in the development of HBV peptide therapeutics and vaccine compositions, methods to circumvent this potential limitation are used. A sequential restimulation of cytotoxic T cells is employed in the present invention to identify and select T cells with a higher affinity for naturally processed antigen than for a synthetic peptide. Short term cytotoxic T lymphocyte lines are established by restimulating activated PBL. Cells stimulated with peptide are restimulated with peptide and recombinant or native HBV antigen, e.g., HBcAg, HBsAg, HBpol, or HBx. Cells having activity are also stimulated with an appropriate T cell mitogen, e.g., phytohemagglutinin (PHA). The restimulated cells are provided with irradiated allogeneic PBLs as an antigen nonspecific source of T cell help, and HBV antigen. To selectively expand the population of cytotoxic T lymphocytes that recognize native HBV antigen and to establish long term lines, PBL from a patient are first stimulated with peptide and recombinant or native HBV antigen, followed by restimulation with HLA-matched B lymphoblastoid cells that stably express the corresponding HBV antigen polypeptide. The cell lines are re-confirmed for the ability to recognize endogenously synthesized antigen using autologous and allogeneic B-lymphoblastoid or other cells transfected or infected with appropriate antigen.

Having identified different peptides of the invention which contribute to inducing anti-HBV cytotoxic T lymphocyte responses in one or more patients or HLA types, in some instances it may be desirable to join two or more peptides in a composition. The peptides in the composition can be identical or different, and together they should provide equivalent or greater biological activity than the parent peptide(s). For example, using the methods described herein, two or more peptides may define different or overlapping cytotoxic T lymphocyte epitopes from a particular region, e.g., the $HBc_{11-27}$ and $HBc_{19-27}$ peptides, which peptides can be combined in a "cocktail" to provide enhanced immunogenicity for cytotoxic T lymphocyte responses. Peptides of one region can be combined with peptides of other HBV regions, from the same or different HBV protein, particularly when a second or subsequent peptide has a MHC restriction element different from the first. This composition can be used to effectively broaden the immunological coverage provided by therapeutic, vaccine or diagnostic methods and compositions of the invention among a diverse population. For example, the different frequencies of HLA alleles among prevalent ethnic groups (caucasian, asian and african blacks) are shown in Table I below. Therapeutic or vaccine compositions of the invention may be formulated to provide potential therapy or immunity to as high a percentage of a population as possible. Thus, inclusion of the $HBc_{141-151}$ CTL epitope with a peptide derived from $HBc_{8-27}$ in a therapeutic or vaccine could benefit as many as 57% of the 300 million people chronically infected with HBV throughout the world.

TABLE I

| HLA ALLELE FREQUENCIES AMONG PREVALENT ETHNIC GROUPS | | | | |
|---|---|---|---|---|
| HLA Allele | EUC | NAC | AFR | JPN |
| A2 | 45.3 | 46.6 | 27.3 | 43.2 |
| A29 | 7.4 | 8.1 | 12.3 | 0.4 |
| A31 | 5.4 | 6.2 | 4.4 | 15.3 |
| A32 | 8.8 | 7.1 | 3 | 0.1 |
| A33 | 3.3 | 3.4 | 9 | 13.1 |
| A28* | 7.7 | 9.9 | 16.6 | 1.1 |

Abbreviations: EUC, European Caucasian; NAC, North American Caucasian; AFR, African blacks, JPN, Japanese. A28 represents the two alleles Aw68 and Aw69

The peptides of the invention can be combined via linkage to form polymers (multimers), or can be formulated in a composition without linkage, as an admixture. Where the same peptide is linked to itself, thereby forming a homopolymer, a plurality of repeating epitopic units are presented. When the peptides differ, e.g., a cocktail representing different HBV subtypes, different epitopes within a subtype, different HLA restriction specificities, a peptide which contains T helper epitopes, heteropolymers with repeating units are provided. In addition to covalent linkages, noncovalent linkages capable of forming intermolecular and intrastructural bonds are included.

Linkages for homo- or hetero-polymers or for coupling to carriers can be provided in a variety of ways. For example, cysteine residues can be added at both the amino- and carboxy-termini, where the peptides are covalently bonded via controlled oxidation of the cysteine residues. Also useful are a large number of heterobifunctional agents which generate a disulfide link at one functional group end and a peptide link at the other, including N-succidimidyl-3-(2-pyridyldithio) proprionate (SPDP). This reagent creates a disulfide linkage between itself and a cysteine residue in one protein and an amide linkage through the amino on a lysine or other free amino group in the other. A variety of such disulfide/amide forming agents are known. See, for example, *Immun. Rev.* 62:185 (1982), which is incorporated herein by reference. Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimidomethyl) cyclohexane-1-carboxylic acid and the like. The carboxyl groups can be activated by combining them with succinimide or 1-hydroxy-2-nitro-4-sulfonic acid, sodium salt. A particularly preferred coupling agent is succinimidyl 4-(N-maleimidomethyl)cyclohexane-1-carboxylate (SMCC). It will be understood that linkage should not substantially interfere with either of the linked groups to function as described, e.g., as an HBV cytotoxic T cell determinant, peptide analogs, or T helper determinant.

In another aspect the peptides of the invention can be combined or coupled with other peptides which present HBV T-helper cell epitopes, i.e., epitopes which stimulate T cells that cooperate in the induction of cytotoxic T cells to HBV. The T-helper cells can be either the T-helper 1 or T-helper 2 phenotype, for example. T-helper epitopes from HBV sequences have been identified at $HBc_{1-20}$ (Seq. ID No. 34), having the sequence: Met-Asp-Ile-Asp-Pro-Tyr-Lys-Glu-Phe-Gly-Ala-Thr-Val-Glu-Leu-Leu-Ser-Phe-Leu-Pro. Other T-helper epitopes are provided by peptides from the region $HBc_{50-69}$ (SEQ. ID No. 35), having the sequence Pro-His-His-Tyr -Ala-Leu-Arg-Gln-Ala-Ile-Leu-Cys-Trp-Gly-Glu-Leu-Met-Tyr-Leu-Ala, and from the region of $HBc_{100-139}$ (SEQ. ID No. 36), including $HBc_{100-119}$ having the sequence Leu-Leu-Trp-Phe-His-Ile-Ser-Cys-Leu-Thr-Phe-Gly-Arg-Glu-Thr-Val-Ile-Glu-Tyr-Leu (where $Ile_{116}$ is Leu in the HBV adw subtype), $HBc_{117-131}$ (SEQ. ID No. 37) having the sequence Glu-Tyr-Leu-Val-Ser-Phe-Gly-Val-Trp-Ile-Arg-Thr-Pro-Pro-Ala, and peptide $HBc_{120-139}$ having the sequence Val-Ser-Phe-Gly-Val-Trp-Ile-Arg-Thr-Pro-Pro-Ala-Tyr-Arg-Pro-Pro-Asn-Ala-Pro-Ile. See, Ferrari et al., *J. Clin. Invest.* 88:214–222 (1991), and U.S. Pat. No. 4,882,145, each incorporated herein by reference.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis,* 2d. ed., Pierce Chemical Co. (1984); Tam et al., *J. Am. Chem, Soc.* 105:6442 (1983); Merrifield, *Science* 232:341–347 (1986); and Barany and Merrifield, *The Peptides,* Gross and Meienhofer, eds., Academic Press, New York, pp. 1–284 (1979), each of which is incorporated herein by reference.

Alternatively, recombinant DNA technology may be employed wherein a nucleotide sequence which encodes a peptide of interest is inserted into an expression vector, transformed or transfected into an appropriate host cell and cultivated under conditions suitable for expression. These procedures are generally known in the art, as described generally in Sambrook et al., *Molecular Cloning, A Laboratory Manual,* Cold Spring Harbor Press, Cold Spring Harbor, N.Y. (1982), and Ausubel et al., (ed.) *Current Protocols in Molecular Biology,* John Wiley and Sons, Inc., New York (1987), and U.S. Pat. Nos. 4,237,224, 4,273,875, 4,431,739, 4,363,877 and 4,428,941, for example, whose disclosures are each incorporated herein by reference. Thus, fusion proteins which comprise one or more peptide sequences of the invention can be used to present the HBV cytotoxic T cell determinants. For example, a recombinant core protein is prepared in which the HBc amino acid sequence is altered so as to more effectively present epitopes of peptide regions described herein to stimulate a cytotoxic T lymphocyte response. By this means a polypeptide is used which incorporates several T cell epitopes.

As the coding sequence for peptides of the length contemplated herein can be synthesized by chemical techniques, for example, the phosphotriester method of Matteucci et al., *J. Am. Chem. Soc.* 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Yeast or mammalian cell hosts may also be used, employing suitable vectors and control sequences.

The peptides of the present invention and pharmaceutical and vaccine compositions thereof are useful for administration to mammals, particularly humans, to treat and/or prevent HBV infection. As the peptides are used to stimulate cytotoxic T-lymphocyte responses to HBV infected cells, the compositions can be used to treat or prevent acute and/or chronic HBV infection.

For pharmaceutical compositions, the peptides of the invention as described above will be administered to an individual already infected with HBV. Those in the incubation phase or the acute phase of infection can be treated with the immunogenic peptides separately or in conjunction with other treatments, as appropriate. In therapeutic applications, compositions are administered to a patient in an amount sufficient to elicit an effective cytotoxic T lymphocyte response to HBV and to cure or at least partially arrest its symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range from about 1 $\mu$g to about 2,000 mg of peptide for a 70 kg patient, with dosages of from about 10 $\mu$g to about 100 mg of peptide being more commonly used, followed by booster dosages from about 1 $\mu$g to about 1 mg of peptide over weeks to months, depending on a patient's CTL response, as determined by measuring HBV-specific CTL activity in PBLs obtained from the patient. It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

Single or multiple administrations of the compositions can be carried out with dose levels and pattern being selected by the treating physician. In any event, the pharmaceutical formulations should provide a quantity of cytotoxic T-lymphocyte stimulatory peptides of the invention sufficient to effectively treat the patient.

For therapeutic use, administration should begin at the first sign of HBV infection or shortly after diagnosis in cases of acute infection, and continue until at least symptoms are substantially abated and for a period thereafter. In well established and chronic cases, loading doses followed by maintenance or booster doses may be required. The elicitation of an effective cytotoxic T lymphocyte response to HBV during treatment of acute hepatitis will minimize the possibility of subsequent development of chronic hepatitis, HBV carrier stage, and ensuing hepatocellular carcinoma.

Treatment of an infected individual with the compositions of the invention may hasten resolution of the infection in acutely infected individuals, about 90% of whom are capable of resolving the infection naturally. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

The peptide compositions can also be used for the treatment of chronic hepatitis and to stimulate the immune system of carriers to substantially reduce or even eliminate virus-infected cells. Those with chronic hepatitis can be identified as testing positive for virus from about 3–6 months after infection. As individuals may develop chronic HBV infection because of an inadequate (or absent) cytotoxic T lymphocyte response during the acute phase of their infection, it is important to provide an amount of immunopotentiating peptide in a formulation and mode of administration sufficient to effectively stimulate a cytotoxic T cell response. Thus, for treatment of chronic hepatitis, a representative dose is in the range of about 1 $\mu$g to 1,000 mg, preferably about 5 $\mu$g to 100 mg for a 70 kg patient per dose. Administration should continue until at least clinical symptoms or laboratory indicators indicate that the HBV infection has been eliminated or substantially abated and for a period thereafter. Immunizing doses followed by maintenance or booster doses at established intervals, e.g., from one to four weeks, may be required, possibly for a prolonged period of time, as necessary to resolve the infection. For the treatment of chronic and carrier HBV infection it may also be desirable to combine the CTL peptides with other peptides or proteins that induce immune response to other HBV antigens.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the cytotoxic T-lymphocyte stimulatory peptides dissolved or suspended in an acceptable carrier, preferably an aqueous carriers may be used, aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

In some embodiments it may be desirable to include in the pharmaceutical composition at least one component which primes CTL. Lipids have been identified which are capable of priming CTL in vivo against viral antigens, e.g., tripalmitoyl-S-glycerylcysteinly-seryl-serine ($P_3CSS$), which can effectively prime virus specific cytotoxic T lymphocytes when covalently attached to an appropriate peptide. See, Deres et al., *Nature* 342:561–564 (1989), incorporated herein by reference. Peptides of the invention can be coupled to $P_3CSS$, for example, and the lipopeptide administered to an individual to specifically prime a cytotoxic T lymphocyte response to HBV. Further, as the induction of neutralizing antibodies can also be primed with $P_3CSS$ conjugated to a peptide which displays an appropriate epitope, e.g., HBsAg epitopes, the two compositions can be combined to more effectively elicit both humoral and cell-mediated responses to HBV infection.

The concentration of cytotoxic T-lymphocyte stimulatory peptides of the invention in the pharmaceutical formulations can vary widely, i.e., from less than about 1%, usually at or at least about 10% to as much as 20 to 50% or more by weight, and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 100 mg of peptide. Actual methods for preparing parenterally administrable compounds will be known or apparent to those skilled in the art and are described in more detail in for example, *Remington's Pharmaceutical Science,* 17th ed., Mack Publishing Company, Easton, Pa. (1985), which is incorporated herein by reference.

The peptides of the invention may also be administered via liposomes, which serve to target the peptides to a particular tissue, such as lymphoid tissue or HBV-infected hepatic cells. Liposomes can also be used to increase the half-life of the peptide composition. Liposomes useful in the present invention include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor, prevalent among lymphoid cells, such as monoclonal antibodies which bind to the CD45 antigen, or with other therapeutic or immunogenic compositions. Thus, liposomes filled with a desired peptide of the invention can be directed to the site of lymphoid or hepatic cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019,369, incorporated herein by reference. For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, the mode of administration, the peptide being delivered, the stage of disease being treated, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, the cytotoxic T-lymphocyte stimulatory peptides are preferably supplied in finely divided form along with a surfactant and propellant. Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included as desired, e.g., lecithin for intranasal delivery.

In another aspect the present invention is directed to vaccines which contain as an active ingredient an immunogenically effective amount of a cytotoxic T-lymphocyte stimulating peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or cytotoxic T cells that react with different antigenic determinants of HBV. Useful carriers are well known in the art, and include, e.g., keyhole limpet hemocyanin, thyroglobulin, albumins such as human serum albumin, tetanus toxoid, polyamino acids such as poly(D-lysine:D-glutamic acid), and the like. The vaccines can also contain a physiologically tolerable (acceptable) diluent such as water, phosphate buffered saline, or saline, and further typically include an adjuvant. Adjuvants such as incomplete Freund'si adjuvant, aluminum phosphate, aluminum hydroxide, or alum are materials well known in the art. And, as mentioned above, cytotoxic T lymphocyte responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amounts of cytotoxic T-lymphocytes specific for HBV antigen, and the host becomes at least partially immune to HBV infection, or resistant to developing chronic HBV infection.

Vaccine compositions containing the peptides of the invention are administered to a patient susceptible to or otherwise at risk of HBV infection to enhance the patient's own immune response capabilities. Such an amount is defined to be a "immunogenically effective dose." In this use, the precise amounts again depend on the patient's state of health and weight, the mode of administration, the nature of the formulation, etc., but generally range from about 1.0 μg to about 500 mg per 70 kilogram patient, more commonly from about 50 μg to about 200 mg per 70 kg of body weight. The peptides are administered to individuals of an appropriate HLA type, e.g., for vaccine compositions of peptides from the region of HBc19-27, these will be administered to HLA-A2 individuals, and peptides containing the $HBc_{114-151}$ epitopic determinant will be administered to A31 and Aw68 individuals.

In some instances it may be desirable to combine the peptide vaccines of the invention with vaccines which induce neutralizing antibody responses to HBV, particularly to HBV envelope antigens, such as recombinant HBV env-encoded antigens or vaccines prepared from purified plasma preparations obtained from HBV-infected individuals. A variety of HBV vaccine preparations have been described, and are based primarily on HBsAg and polypeptide fragments thereof. For examples of vaccines which can be formulated with the peptides of the present invention, see generally, EP 154,902 and EP 291,586, and U.S. Pat. Nos. 4,565,697, 4,624,918, 4,599,230, 4,599,231, 4,803,164, 4,882,145, 4,977,092, 5,017,558 and 5,019,386, each being incorporated herein by reference. The vaccines can be combined and administered concurrently, or as separate preparations.

For therapeutic or immunization purposes, the peptides of the invention can also be expressed by attenuated viral hosts, such as vaccinia. This approach involves the use of vaccinia virus as a vector to express nucleotide sequences that encode the HBV peptides of the invention. Upon introduction into an acutely or chronically HBV-infected host or into a non-infected host, the recombinant vaccinia virus expresses the HBV peptide and thereby elicits a host cytotoxic T lymphocyte response to HBV. Vaccinia vectors and methods useful in immunization protocols are described in, e.g., U.S. Pat. No. 4,722,848, incorporated herein by reference. Another vector is BCG (bacille Calmette Guerin). BCG vectors are described in Stover et al. (*Nature* 351:456–460 (1991)) which is incorporated herein by reference. A wide variety of other vectors useful for therapeutic administration or immunization of the peptides of the invention, e.g., *Salmonella typhi* vectors and the like, will be apparent to those skilled in the art from the description herein.

The compositions and methods of the claimed invention may be employed for ex vivo therapy. By ex vivo therapy is meant that therapeutic or immunogenic manipulations are performed outside the body. For example, lymphocytes or other target cells may be removed from a patient and treated with high doses of the subject peptides, providing a stimulatory concentration of peptide in the cell medium far in excess of levels which could be accomplished or tolerated by the patient. Following treatment to stimulate the CTLs, the cells are returned to the host to treat the HBV infection. The host's cells may also be exposed to vectors which carry genes encoding the peptides, as described above.. Once transfected with the vectors, the cells may be propagated in vitro or returned to the patient. The cells which are propagated in vitro may be returned to the patient after reaching a predetermined cell density.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic HBV infection.

The following examples are offered by way of illustration, not by way of limitation.

EXAMPLE I

Identification of CTL-Specific HBc Epitopes

Three patients (M. B., J. P. and J. V.) were studied during the acute phase of viral hepatitis type B. Diagnosis of acute hepatitis was based on the finding of elevated values of SGPT activity (at least 10 times the upper level of the normal; mean SGPT value peak being 2179 IU/L), associated with the detection of IgM anti-HBcAg antibodies in the serum. All patients recovered completely from the illness, with normalization of serum transaminase and clearance of HBsAg. They were antibody negative to δ Ag and to hepatitis C virus. Patient J. P. was A2, A3, B44, B35, Cw4, DR1, DR2, DRw8, and DQw1; V. J. was A2, A11, B44, B62, Cw5, DR4, DRw12; B. M. was A2, B38, B27, DR5, DRw52 and DQw3. Thus, all patients were HLA-A2 positive. Peripheral blood lymphocytes from these patients were analyzed for HBV specific CTL activity either immediately after isolation, after 1 or 2 weeks of stimulation with autologous stimulator cells transfected with HBV expression vectors as described below, or after stimulation with a panel of 4 pools of overlapping synthetic peptides which were 10 to 20 residues long, each comprising 5 to 6 peptides covering the entire HBV nucleocapsid (core and pre-core) region (ayw subtype). The peptides which comprised each pool are shown in FIG. 1.

Peptide-specific CTL were generated from the PBL of the three patients with acute hepatitis as follows. PBL were cultured at $4 \times 10^6$ cells per ml in RPMI 1640 containing 10% AB serum plus either 10 μg/ml of a peptide pool containing the $HBc_{11-27}$ peptide or the HBc11–27 peptide and 1 μg/ml of recombinant (r)HBcAg (Biogen, Geneva, Switzerland), in a 24 well plate (Corning). After 4 days of culture, the cells were re-fed with RPMI 1640 containing 10% FCS and 20 U/ml rIL2 (Hoffman-LaRoche, Basel, Switzerland). In the case of patient V. J. the peptide-primed cells were restimulated after 1 week of culture with $HBc_{11-27}$ peptide and rHBcAg (1 mg/ml) in the presence of autologous irradiated (3500 RAD) PBL as antigen presenting cells. The peptide-primed cells from patient J. P. were restimulated on day 7 with 1 μg/ml of phytohemagglutinin (PHA) in the presence of allogeneic irradiated (7000 RAD) PBL. Cytotoxic activity was assessed after 7 days (patient M. B.) or 14 days (patients V. J. and J. P.) of culture.

Cytotoxic activity was assessed by incubating the stimulated PBL with autologous or allogeneic (HLA-matched or mismatched) $^{51}$Cr-labelled, peptide pulsed (20 μg/ml for 1 hr) BCL cells for 4 hr in round-bottomed 96-well plates at effector to target (E/T) ratios of 100 (M. B.) or 10 (V. J., J. P.). Parental BCL cells not pulsed with peptide served as negative controls. Per cent target cell lysis was calculated from the formula (E-M/T-M)×100, where E=experimental $^{51}$Cr release (cpm); M=$^{51}$Cr release in presence of culture medium (which ranged between 15–25% of total counts); and T=total $^{51}$Cr released by 10% Triton X.

As illustrated in FIG. 2, HBV specific CTL activity was reproducibly observed only following stimulation with the, panel of overlapping nucleocapsid peptides. Peptide specific CTL activity was consistently elicited only with one of the four peptide pools and recognition was limited to a single peptide within that pool, consisting of residues 11–27 of hepatitis B core antigen (HBcAg) of the sequence Ala-Thr-Val-Glu-Leu-Leu-Ser-Phe-Leu-Pro-Ser-Asp-Phe-Phe-Pro-Ser-Val, [SEQ. ID. No. 2], which is conserved among the major subtypes of HBV. This is a dominant epitope in HLA-A2 positive patients with acute viral hepatitis.

Figure 2A:
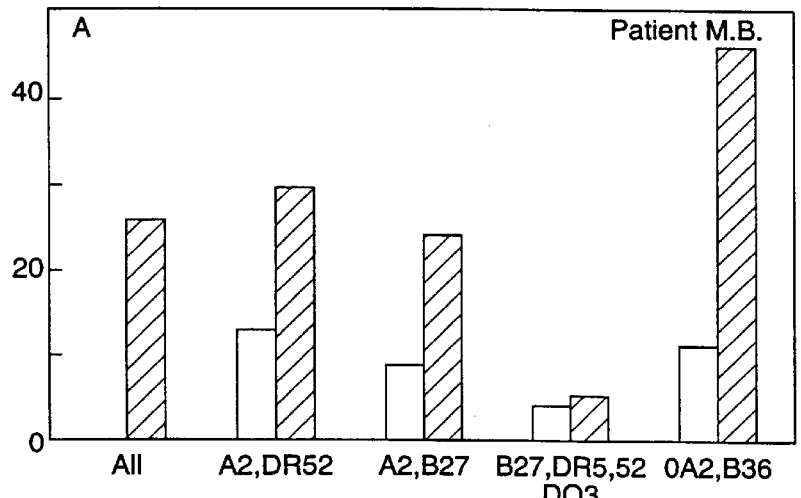
(FIG. 2A), V. J.
Figure 2B:
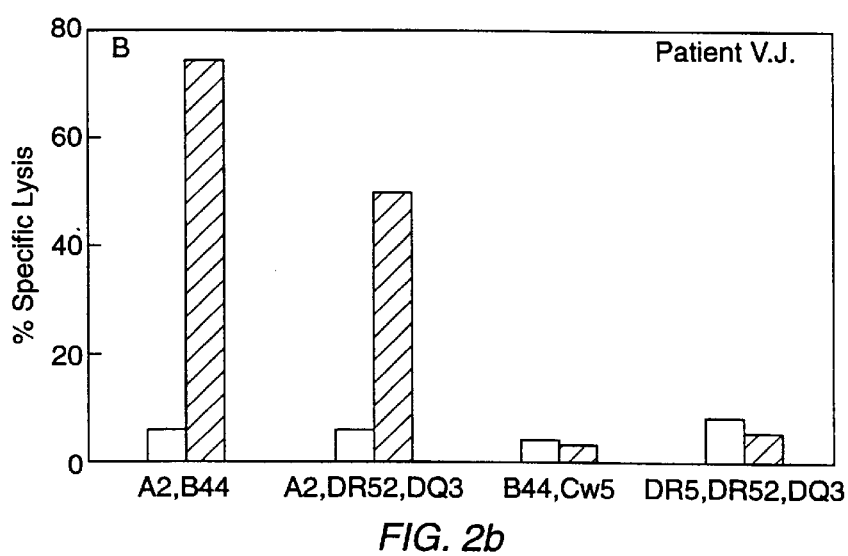
(FIG. 2B) and J. P.
Figure 2C:
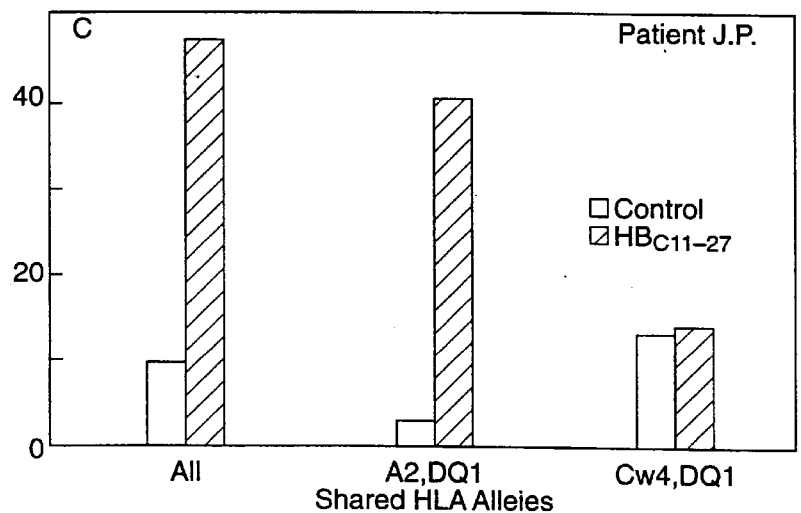
(FIG. 2C) and the HLA-A2 restricted response, where the HLA alleles shared between each patient and target cells are shown.

Following one week of stimulation with a peptide mixture containing the $HBc_{11-27}$ determinant, lymphocytes from patient M. B. specifically lysed autologous and HLA-A2 matched B-lymphoblastoid cells (BCL) incubated with the peptide (FIG. 2A). A peptide-specific CTL line was also established from PBL derived from patient V. J. (FIG. 2B) by stimulation with the $HBc_{11-27}$ peptide plus recombinant HBV-core antigen, as a source of antigen specific T cell help (Ferrari et al., *J. Immunol*, 145:3422 (1990) for expansion of the $HBc_{11-27}$ specific CTL, followed by restimulation by the same reagents. Similarly, an $HBc_{11-27}$ specific CTL line was established using PBL from patient J. P. (FIG. 2C) by 1 week of peptide and HBcAg stimulation followed by restimulation with PHA and irradiated allogenic PBL as an antigen non-specific source of T cell help. The procedures resulted in establishment of short term CTL lines that were able to lyse peptide-pulsed autologous and allogeneic HLA-A2 positive target cells, but not HLA-A2 mismatched targets, demonstrating that peptide recognition by the CTL was HLA-A2 restricted.

In separate experiments performed as generally described herein, peptides $HBc_{19-27}$ and HBc8-27 were found to specifically stimulate CTL activity in a manner restricted by at least HLA-A2. In other experiments peptides $HBc_{28-47}$ and $HBc_{111-125}$ were shown to specifically stimulate CTL activity against HBV antigens, and peptide $HBc_{140-154}$ stimulated CTL activity in a manner that appeared to be restricted to at least HLA-A31.

EXAMPLE II

CTLs Specific for HBc Peptides Recognize Recombinant HBV Core Antigen

The short term, peptide-specific CTL lines from the three patients of Example I were tested for the capacity to recognize endogenously synthesized HBV core antigen using autologous and allogenic BCL targets transfected or infected with the HBV core expression vectors.

Two different eukaryotic expression systems were used. Recombinant vaccinia viruses that express either the HBV core (Vcore) or precore (Vprecore) polypeptides (subtype ayw) were used as described in Schlicht and Schaller, *J. Virol.* 63:5399 (1989), incorporated herein by reference. Additionally, EBV-B cells were stably transfected with a panel of recombinant plasmids which express the HBV core (EBO-core) and envelope (EBO-env) polypeptide (subtype ayw) in an Epstein-Barr virus based vector (EBOpLPP) as described in Canfield et al., *Mol. Cell. Biol.* 10:1367 (1990), incorporated herein by reference.

Effector cells derived from patient M. B. and J. P. after 7 and 14 days of stimulation as described in Example I were incubated with target cells for 4 hours at E/T ratios of 100:1 and 10:1, respectively. Before $^{51}$Cr-labeling, BCL targets were either infected with recombinant vaccinia viruses (FIG. 3, Panel A) at a multiplicity of infection of 20 for 14 hours, to allow the expression of HBV-encoded gene products (Vw=vaccinia wild type, Vcore=vaccinia carrying the HBcAg open reading frame) or, for patient J. P., transfected with EBV-based episomal vectors (Panel B) previously shown to induce efficient expression of either envelope (EBO-env) or nucleocapsid antigen (EBO-core).

Figure 3:
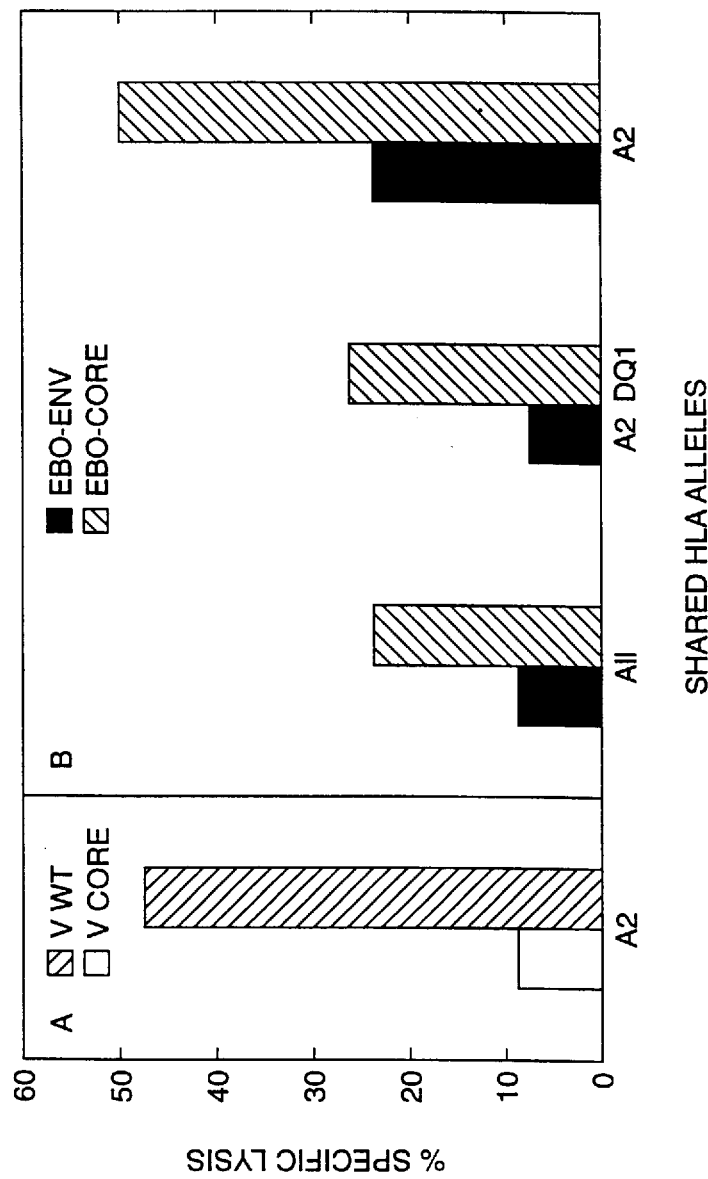
FIG. 3 shows the recognition of endogenously synthesized HBV nucleocapsid antigen by peptide specific CTL, with effector cells derived from patient M. B. (Panel A) and J. P. (Panel B), where Vw=vaccinia wild type, Vcore=vaccinia carrying the HBcAg open reading frame, EBO-env is an EBV-based episomal vector expressing HBV envelope, and EBO-core is an EBV-based episomal vector expressing HBV nucleocapsid antigen.

As shown in FIG. 3, the CTL specifically lysed autologous BCL that transiently or stably expressed the HBV core polypeptide but not the HBV envelope antigens. By employing a panel of HLA-A2 matched and mismatched allogenic target cells, specific recognition of endogenously synthesized native (recombinant) core antigen was also to be HLA-A2 restricted.

EXAMPLE III

Sequential Stimulation with Nucleocapsid Transfectants Produces Anti-HBV CTL of High Affinity Stimulation with peptide antigen can induce CTL with low affinity for the corresponding endogenous protein (Carbone et al., *J. Exp. Med.* 167:1767 (1988)), such that repetitive peptide stimulation may yield CTL that recognize the synthetic peptide but not native antigen. In order to selectively expand the population of CTL that recognize native nucleocapsid antigen and to establish long term lines for further analysis, PBL from patient J. V. were stimulated for 1 week with peptide $HBc_{11-27}$ plus recombinant HBcAg, following which the activated PBL were restimulated with HLA-matched transfected BCL that stably expressed the HBV nucleocapsid polypeptide.

Figure 4A:
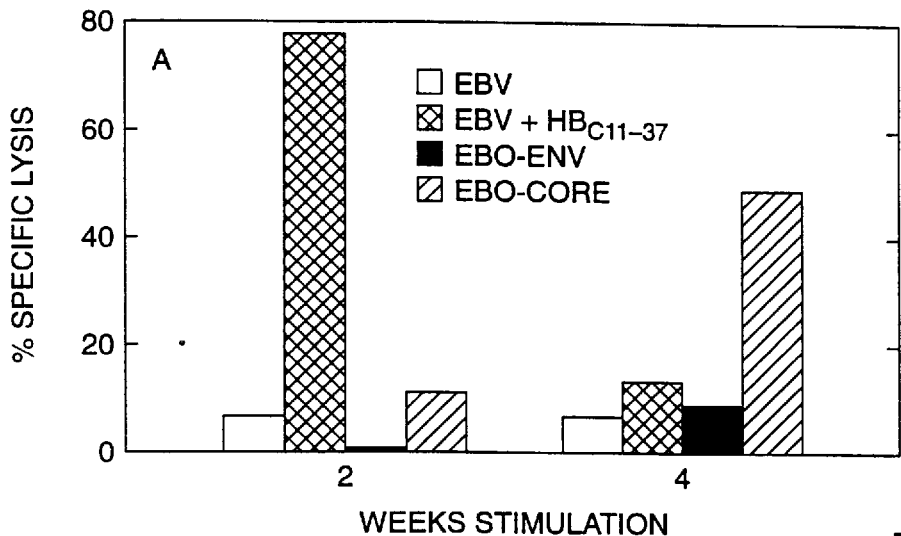
FIGS. 4A–4C illustrates the selective expansion of HLA-A2 restricted CTL that recognize endogenously synthesized HBV nucleocapsid antigen, where Panel A shows cytolytic activity by CTL line V. J. against HLA-A2 matched BCL either prepulsed with HBcl$_{11-27}$ peptide or cultured in medium alone and against EBO-transfectants expressing nucleocapsid or envelope antigens, with experiments performed before (two weeks) and after (four weeks) two rounds of stimulation with EBO-core transfectants; Panel B shows recognition by CTL line V. J. during weeks 3, 4 and 5 of culture after 1, 2 or 3 sequential rounds of stimulation with EBO-core transfectants; and Panel C shows CTL activity toward HLA-A2 matched and mismatched BCL targets infected with recombinant vaccinia viruses after 5 weeks of culture.

The details were as follows. After two weeks of stimulation with $HBc_{113-27}$ peptide and rHBcAg, the peptide-specific CTL line J. V. (FIG. 2B) was further restimulated every seven days with irradiated (7000 RAD) HLA class I-matched EBO-core transfectants ($1 \times 10^6$ /ml) plus autologous irradiated (3000 RAD) PBL ($5 \times 10^6$/ml) and rHBcAg (1 mg/ml in RPMI+10% FCS+20 U/ml of rIL2. As shown in FIG. 4A, the cytolytic activity was tested against HLA-A2 matched BCL either prepulsed with $HBc_{11-27}$ peptide or cultured in medium alone and against EBO transfectants expressing endogenously synthesized nucleocapsid or envelope antigens. Experiments were performed before (2 weeks) and after (4 weeks) two rounds of stimulation with EBO-core transfectants (E/T ratio=20:1).

As shown in FIG. 4A, prior to restimulation the CTL displayed a high level of cytotoxicity towards peptide pulsed targets with only minimal specific killing of target cells expressing endogenously synthesized antigen. Following restimulation with the nucleocapsid transfectant, T cells displayed increased killing of targets that express endogenously synthesized antigen concomitant with a decrease in killing of peptide pulsed target cells. FIG. 4A.

Figure 4B:
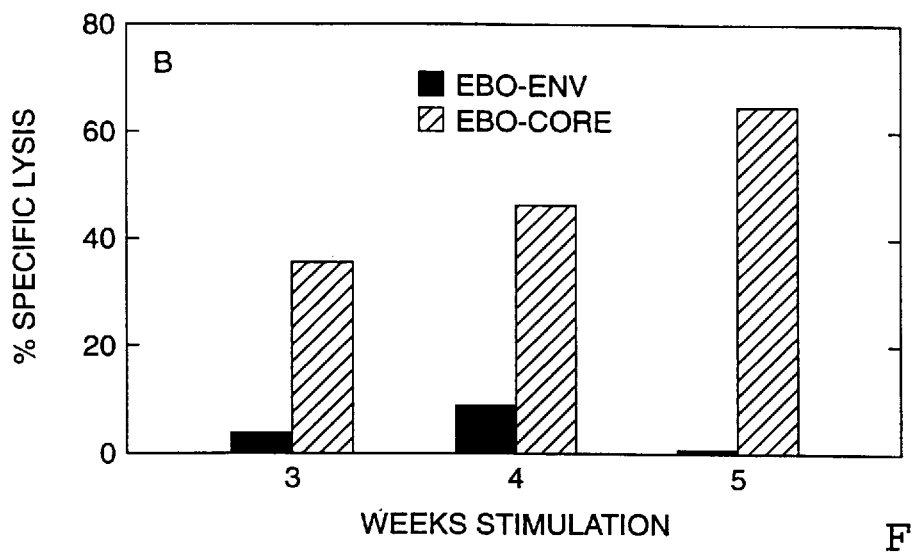

Recognition of endogenously synthesized antigen increased progressively with time following restimulation, as shown in FIG. 4B. This panel shows the recognition of endogenously synthesized HBV nucleocapsid antigens by CTL line V. J. during weeks 3, 4 and 5 of culture after 1, 2 or 3 sequential rounds of stimulation with EBO-core transfectants (E/T=20:1). These results suggest that CTL with higher affinity for the endogenously produced antigen were being selected.

Figure 4C:
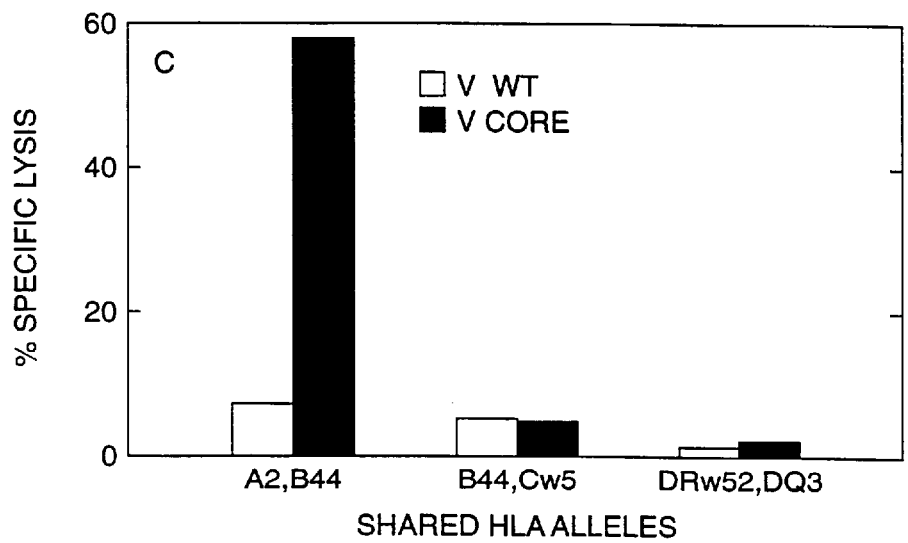

FIG. 4C shows the cytolytic activity towards HLA-A2 matched and mismatched BCL targets infected with recombinant vaccinia viruses (as described in Example II) after 5 weeks of culture (E/T=50:1).

These results suggest that naturally processed nucleocapsid antigen is similar, but not identical, to the synthetic $HBC_{11-27}$ peptide used to expand the CTL precursor population. The fact that this sequential stimulation worked so well, when many prior attempts to detect HBV specific CTL in freshly isolated PBL without prior stimulation failed, suggests that the HBV specific CTL precursors are present in the peripheral blood compartment at very low frequency. The failure to induce HBc specific CTL solely by in vitro stimulation with stably transfected autologous BCL, which served as excellent target cells, suggest that higher epitope densities are generally required for CTL induction compared with the density required for lysis.

The phenotype of the $HBc_{11-27}$ specific CTL was assessed by incubating HBV core transfectants and nucleocapsid specific CTL line from patient V. J. with antibodies specific for the differentiation markers CD4 and CD8. The V. J. CTL line was tested against A2-positive EBO-core and EBO-env targets in the presence of saturating concentrations (0.6 µg/ml) of $IgG_1$ monoclonal antibodies anti-Leu-3a (CD4) and anti-Leu-2a (CD8), obtained from Becton-Dickinson. Antibodies were added to the culture at the initiation of the chromium release assay. Antigen specific lysis was blocked by 80% with antibodies to CD8 whereas no inhibition was obtained with antibodies to CD4. These results demonstrate that the $HBc_{11-27}$ specific, HLA-A2 restricted CTL activity is mediated exclusively by CD8 positive cells.

Figure 5:
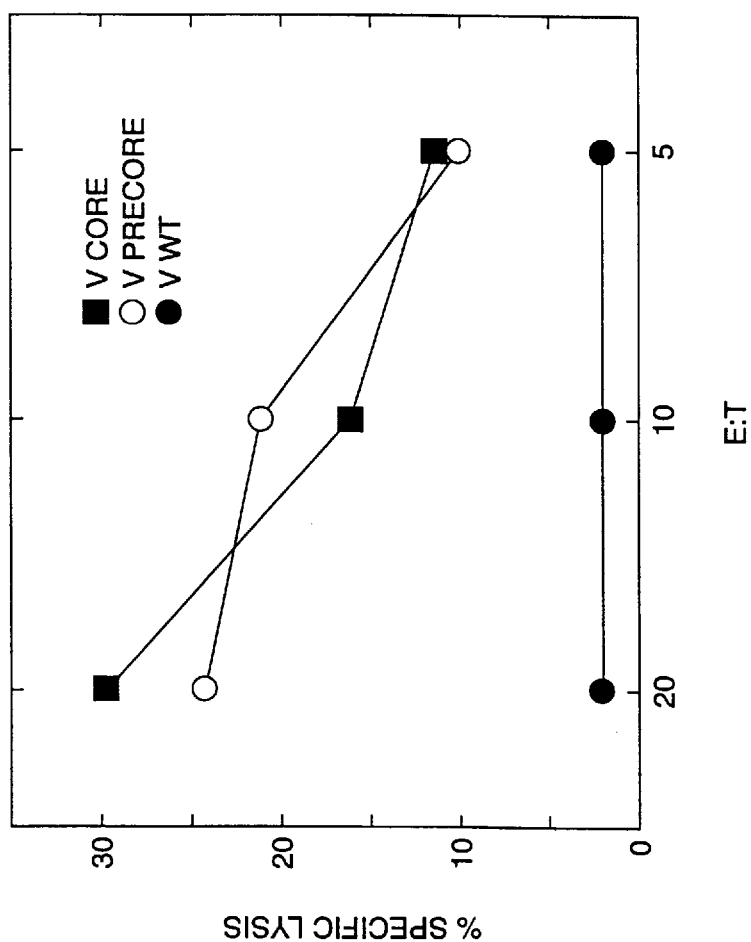
FIG. 5 illustrates HBc$_{11-27}$ specific CTL recognition of an epitope shared by HBV core and precore region encoded polypeptides expressed by HLA-A2 BCL infected with recombinant vaccinia, where CTL line J. V. was used as a source of effector cells.

EXAMPLE IV $HBc_{11-27}$ Specific CTL Recognize an Epitope Shared by the HBV Core and Precore Region Encoded Polypeptides The $HBc_{11-27}$ epitope(s) are located within two independent nucleocapsid polypeptides (core and precore), one of which (precore) contains an amino terminal signal sequence that leads to its translocation into the endoplasmic reticulum and secretion as hepatitis B e antigen (HBeAg) (Uy et al., Virology 155:89 (1986); Roosinck et al., Mol. Cell, Biol, 6:1393 (1986); and Standring et al., Proc, Natl. Acad. Sci. USA 85:8405 (1988)). The core polypeptide is primarily a cytoplasmic and nuclear protein (HBcAg) and is not secreted (Roosinck and Siddiqui, J. Virol, 61:955 (1987), and McLachlan et al., J. Virol, 61:683 (1987)). To determine whether one or both polypeptides serve to generate the HLA-A2 restricted $HBc_{11-27}$ specific CTL epitope(s), HLA-A2 positive BCL target cells were infected with recombinant vaccinia viruses engineered to express the native core and precore polypeptides independently, as described in Example II. CTL line J. V. was used as a source of effector cells in a 4 hr $^{51}Cr$ release assay at the E:T ratio indicated in FIG. 5.

The results showed that both target cell lines were killed to an equivalent degree by $HBc_{11-27}$ specific CTL line from patient V. J., demonstrating that HBcAg and HBeAg shared a common intracellular processing pathway and that they are cross-reactive at the HLA class I restricted CTL level.

EXAMPLE V

Immunodominance of the $HBC_{11-27}$ CTL Epitope in HLA-A2 Haplotype Individuals To assess the immunodominance in the HLA-A2 haplotype of the CTL epitope(s) contained in peptide $HBc_{11-27}$, eight additional subjects with self-limited acute hepatitis B infection, four patients with chronic active hepatitis B, and eight healthy subjects without evidence of previous exposure to HBV (all HLA-A2 positive) were repeatedly tested.

All of the acute patients serially studied (every 7–10 days) during the symptomatic and the recovery periods of the disease efficiently recognized autologous target cells pulsed with peptide $HBc_{11-27}$ as well as with MIX4 (FIG. 1). Restriction experiments performed with MIX4-stimulated PBMC from four of them confirmed that CTL recognition of peptide $HBc_{11-27}$ was HLA-A2 restricted. Patient to patient variations in the pattern of response to the peptide were observed during the course of the illness. The cytolytic activity was generally detectable during the icteric phase when transaminase values were high; in some patients the response was long-lasting, being still detectable when GPT levels had already become normal, and in other subjects the lytic activity became undetectable 2 or 3 weeks after the transaminase peak when GPT levels were still slightly altered. The lack of a constant association between CTL activity and SGPT levels suggested the peripheral blood compartment only partially reflected immune events taking place in the liver at the site of antigen synthesis and cellular injury.

Three of the four chronic patients (each one tested two or three times, following the same experimental protocol used for the acute patients), did not show cytolytic activity against autologous macrophages pulsed with peptide $HBc_{11-27}$, while one patient displayed detectable, though very low levels of cytotoxicity against the relevant peptide sequence. The lytic activity against peptide $HBc_{11-27}$ was not detectable in normal HLA-A2 positive control subjects, demonstrating that this response was not due to in vitro priming and that peptide stimulation selectively expanded a specific T cell population pre-primed in vivo by HBV infection.

These results show a clear correlation between the CTL response to core peptide $HBc_{11-27}$ and acute HBV infection in patients who succeed in clearing the virus.

EXAMPLE VI

Identification of CTL Activity Restricted to HLA-A31 and Aw68

This Example describes the identification of a CTL response to an HBV nucleocapsid epitope that is restricted by two independent HLA class I molecules, HLA-A31 and HLA-Aw68.

Six patients, five male and one female, with acute hepatitis B, and nine normal blood donors were studied (Table II). The diagnosis of acute hepatitis B was based on standard diagnostic criteria including clinical and biochemical evidence of severe liver cell injury with alanine aminotransferase (ALT) activity at least 20 fold higher than the upper limits of normal, together with serological evidence of acute HBV infection, including hepatitis surface antigen (HBsAg) and IgM anti HBc antibody (IgM HBc-Ab) and the absence of serological evidence of infection by the hepatitis delta or hepatitis C viruses (using commercially available reagents obtained from Abbott Laboratories, North Chicago, Ill.). All patients recovered completely from the illness, with normalization of serum transaminase and clearance of HBsAg within 4 months of initial diagnosis.

TABLE II

HLA Class of the Patients Studied and of the HLA-A31 and Aw68 Normal Donors Used to Produce Target Cells

| HLA CLASS I | |
|---|---|
| PATIENT | |
| E. W. | A31, Aw68, B35, Cw3, Cw4 |
| H. P. | A2, Aw68, B35, Bw62, Cw3, Cw4 |
| V. T. | A25, A31, B7, BI8 |
| H. F. | A31, Aw68, Bw61, Cw3 |
| Q. M. | Aw36, Aw68, B49, Bw62, Cw1 |
| V. P. | A24, Aw68, B35, Bw67 |
| C. N. | A24, Aw68, Bw60, Cw3 |
| DONOR | |
| a | A1, A31, B17, Bw60 |
| b | A2, A31, B27, B44, Cw1 |
| c | A3, A31, B7, B27 |
| d | A24, A31, B14, B35, Cw4 |
| e | A3, A31, B7 |
| f | A31, Aw68, B35, Bw60 |
| g | A3, Aw68, B7, B44, Cw7 |
| h | A1, Aw68, B8, B38, Cw7 |
| i | A11, Aw68, B35, B44, Cw4 |

PBMC from patients and normal donors were separated on Ficoll-Hypaque density gradients, washed three times in Hanks balanced salt solution (HBSS), resuspended in RPMI 1640 medium supplemented with L-glutamine (2 mM), penicillin (50 U/ml), streptomycin (50 µg/ml), and HEPES (10 mM) containing 10% heat-inactivated human AB serum and plated in 24/well plate at $4 \times 10^6$ cells/well. The synthetic peptides each at 10 µg/ml were added to cell cultures as follows: Mixture 1, core residues 1–20, 20–34, 28–47, 50–69, 70–89, 61–80; Mixture 2, core residues 82–101, 100–119, 120–139, 140–155, 155–169, 169–183; Mixture 3, pre-core residue 20-core residue 2, core residues 50–59, 117–131, 131–145, 111–125; and Mixture 4, core residues 11–27, 91–110, 147–160, 162–176. rHBcAg (Biogen, Geneva, Switzerland) was added at 1 µg/ml to derive the benefit of a helper T cell response within the culture during the first week of stimulation. At day 3, 1 ml of RPMI with 10% human AB serum and rIL2 at 10 U/ml final concentration was added in each well. The cultured PBMC were tested for CTL activity on day 7, and short term CTL lines that displayed CTL activity specific for the peptide mixture used during the first week of stimulation were expanded by restimulation as described below.

HBV core-specific CTL line H1 was generated from patient H. P., initially cultured with peptide Mix 2 plus rHBcAg, by weekly restimulation with $5 \times 10^5$ autologous PBMC irradiated (3000 rads) in RPMI plus 10% human AB serum, rIL2 (20 U/ml) and peptide Mix 2 (first restimulation) or with peptide 140–155 (10 µg/ml) for all subsequent stimulations. CTL line E4 (from patient E. W.) and the CTL lines from 4 additional patients (V. T., H. F., Q. M., C. N.) were established by stimulating PBMC with peptide 140–155 plus rHBcAg for the first week, with weekly restimulation thereafter with peptide 140–155 and rIL2. The PBMC of the normal uninfected controls were stimulated similarly except that in selected instances tetanus toxoid was substituted for rHBc during the first week of stimulation to provide an alternate source of T cell help, since these individuals had not been exposed to HBcAg.

HBV specific CTL clones were generated by limiting dilution at 1 cell/well in 96 well microtiter plates from an HBV specific CTL line E4 (patient E. W). After depletion of CD4 +T cells from the CTL line by incubation with a CD4-specific monoclonal antibody (Becton Dickinson, Mountain View, Calif.) plus complement, the cells were plated in the presence of PHA at 1µg/ml, CD3-specific monoclonal antibody at 0.5µg/ml (Coulter Ismunology, Hialeah, Fla.) rIL-2 (20 U/ml) and irradiated (5000 rads) allogeneic PBMC $10^5$/well. HBV specific clones were restimulated in a 24 well plate with 105 irradiated (9000 rads) autologous transfectants expressing the HBV core region (described above), with $2 \times 10^6$ allogeneic irradiated (3000 rads) PBMC feeder cells per well, in RPMI 1640 medium containing 10% heat inactivated FCS and IL2 20 U/ml.

For target cell lines, autologous and allogeneic EBV-transformed B lymphoblastoid cell lines (LCL) were either purchased from The American Society for Histocompatibility and Immunogenetics (Boston, Mass.) or established from a pool of patients and normal donors as described above. The cells were maintained in RPMI with 10% (vol/vol) heat-inactivated FCS. Short term lines of autologous PBMC blasts were produced by stimulating peripheral blood PBMC with PHA at 1 µg/ml in RPMI with 10% FCS, 10 U/ml rIL2 for 7 days before use as target cells.

Cytotoxicity Assays were performed using target cells of either a) autologous PHA stimulated blasts or allogeneic HLA matched and mismatched B-LCL incubated overnight with synthetic peptides at 10 pg/ml; b) stable B-LCL transfectants described above; or c) B-LCL infected with recombinant vaccinia viruses. Vaccinia infected targets were prepared by infection of $1 \times 10^6$ cells at 50 plaque-forming U/cell on a rocking plate at room temperature for one hour followed by a single wash and overnight incubation at 37°

C. Target cells were then labeled with 100 μCi of $^{51}$Cr for one hour and washed three times with HBSS. Cytolytic activity was determined in a standard 4 hour $^{51}$Cr-release assay using U-bottom 96 well plates containing 5000 targets per well. Stimulated PBMC were tested at E:T ratios between 70–100:1, whereas HBV core specific CTL lines were tested at E:T ratios between 4–50:1, and normal donors stimulated PBMC at E:T ratio of 60:1. All assays were performed in duplicate. Percent cytotoxicity was determined from the formula: 100×[(experimental release−spontaneous release)/(maximum release−spontaneous release)). Maximum release was determined by lysis of targets by detergent (1% Triton X-100, Sigma). Spontaneous release was less than 25% of maximal release in all assays.

Figure 6:
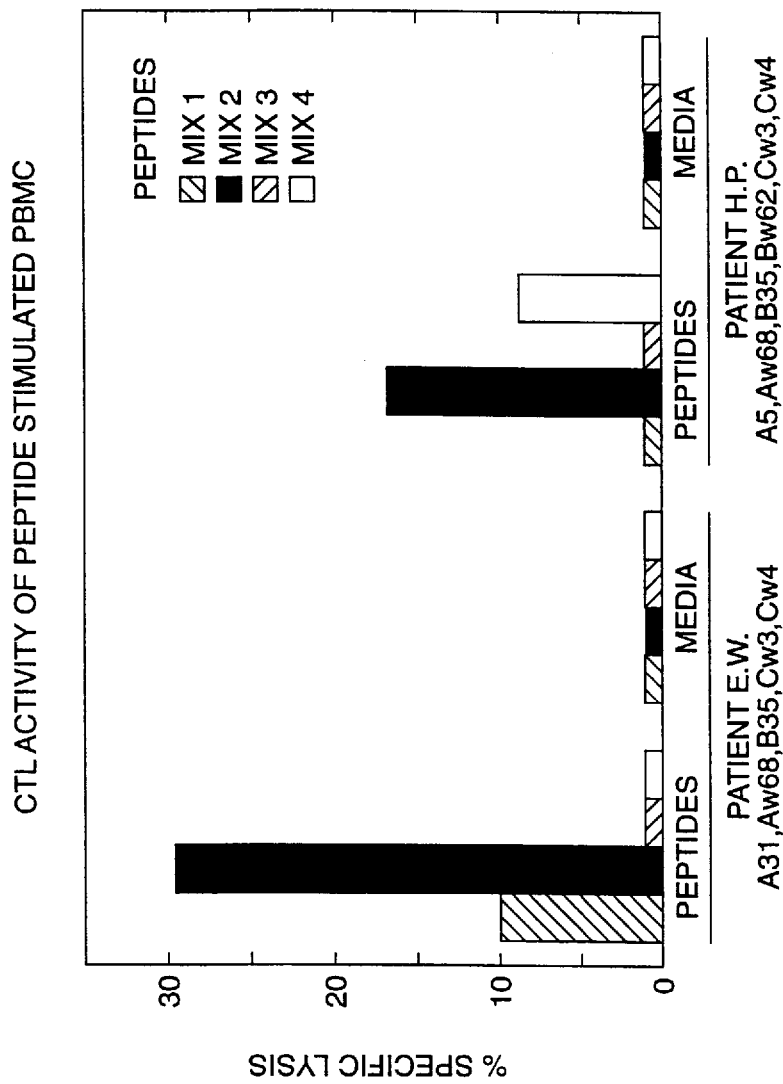
FIG. 6 shows activation of HBV-specific CTL by PBMC stimulation with mixtures of synthetic peptides. Cytolytic activity of PBMC stimulated for one week against autologous targets prepulsed with the same stimulatory mixture or with media only. The E/T ratio used was 70:1 for patient E. W. and 100.1 for patient H. P.
Figure 7A:
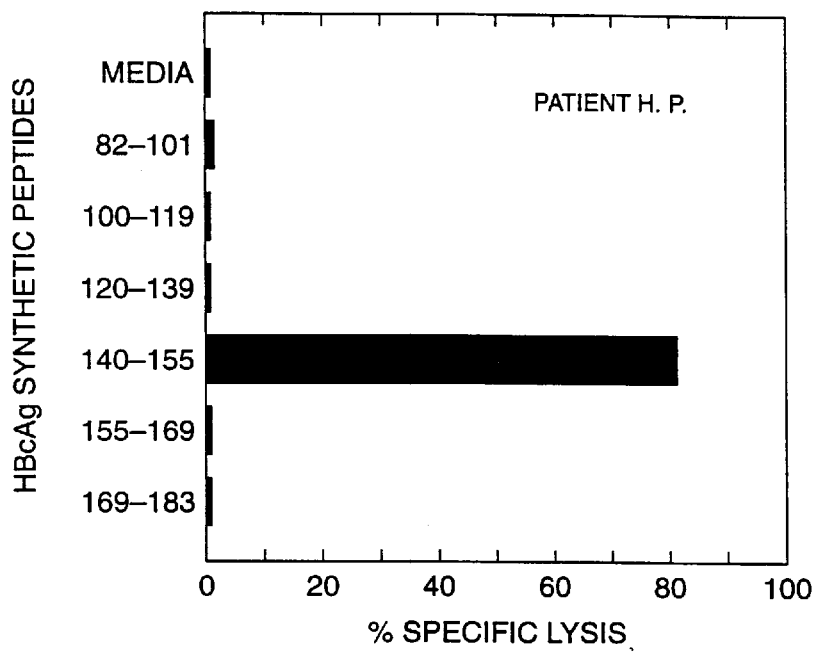
FIGS. 7A–7B confirms that HBcAg 140–155 is the peptide recognized in mixture 2. Cytolytic activity of PBMC stimulated by peptides contained in mixture 2 for the first week and restimulated with the same peptides against autologous target cells prepulsed with the individual peptides of the mixture. The E/t ratio used was 50:1 for patient E. W. and 40:1 for patient H. P.
Figure 7B:
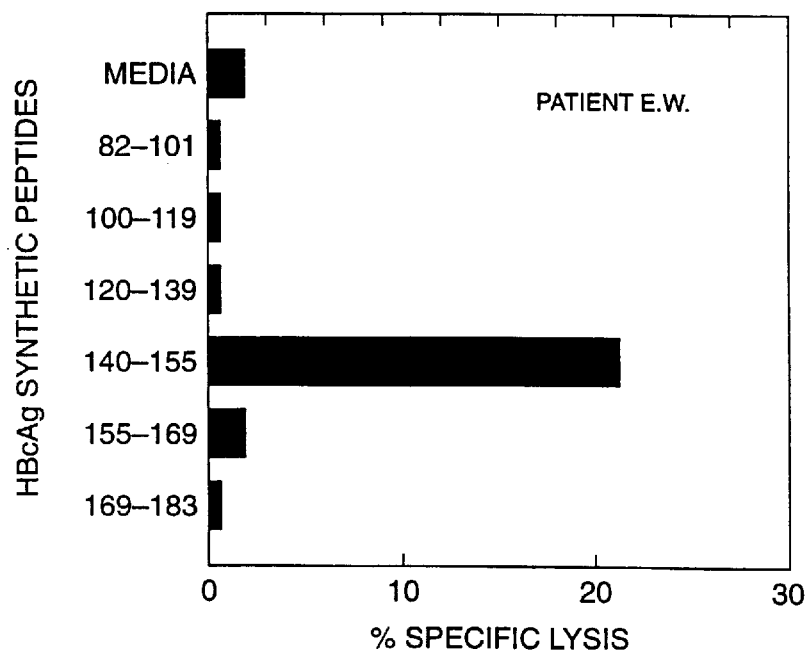

PBMC from 2 patients (E. W. and H. P.) with acute HBV infection were stimulated for 7 days with the peptide mixtures described above and then tested for cytolytic activity against autologous $^{51}$Cr-labeled, PHA-activated blasts prepulsed with the same peptide mixture or with media. Responses were observed to mixture 2 in both patients (FIG. 6). The remaining cells were restimulated for a second week with peptide mixture 2 and the antigenic specificity of the restimulated CTL line was established with autologous PHA activated blast targets prepulsed with the individual peptides contained within the mixture. By this approach, peptide HBcAg 140–155 was shown to be responsible for the CTL activity induced by Mix 2 for both patients (FIG. 7). No cytotoxic activity was observed using unstimulated PBMC of patient E. W. as effectors against autologous B-LCL fed with peptide HBcAg 140–155, suggesting that specific CTL were present at low frequency in the peripheral blood during acute HBV infection. Patient H. P. also displayed a CTL response to Mix 4 (FIG. 6), ultimately shown to be specific for core residues 11–27 and to be restricted by HLA-A2. This demonstrated that multiple, independently restricted CTL responses to non-overlapping CTL epitopes present on the same viral protein were readily detectable during acute HBV infection.

Figure 8:
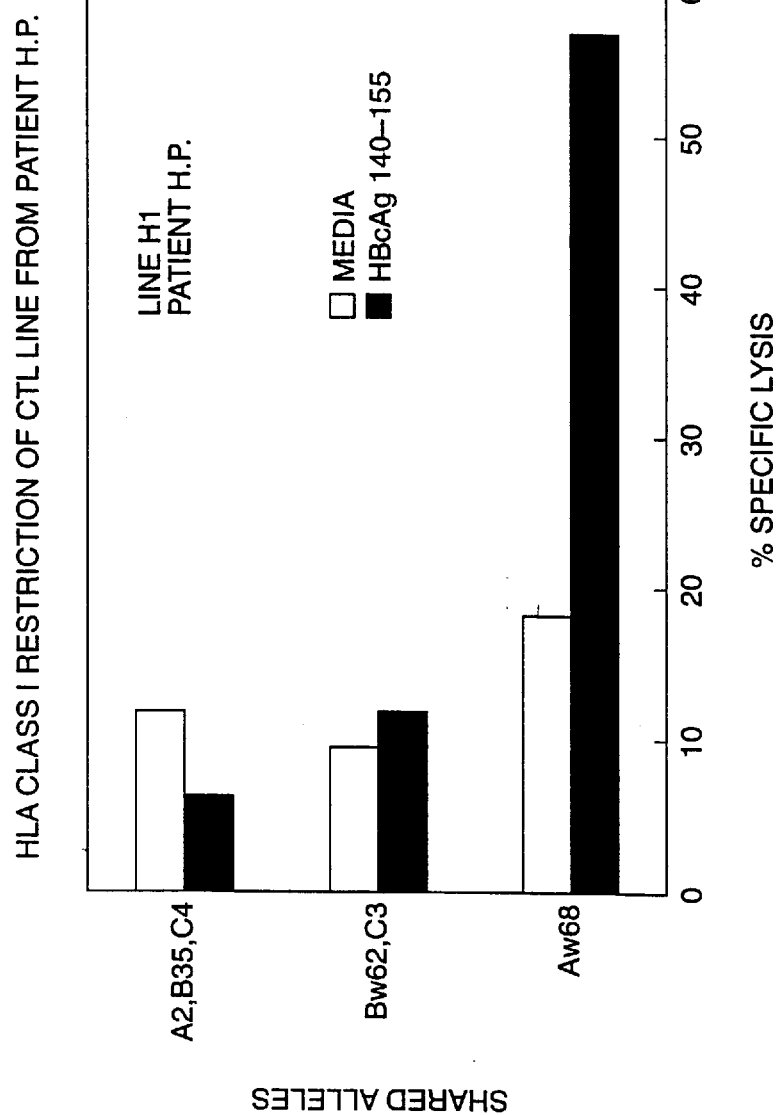
FIG. 8 shows that Aw68 is the restriction element of the HBcAg 140–155 specific CTL response of line H1. Allogeneic target cells were prepulsed with peptide HBcAg140–155 or with media and matched at the level of class I with the effector cells, and completely mismatched at the level of class II. The E/T ratio used was 4:1.

HBcAg 140–155 specific CTL lines were generated by weekly stimulation of PBMC either with Mix 2 or with an active constituent peptide (core residues 140–155). Line E4 (patient E. W.) was started in the presence of rHBcAg and peptide HBcAg 140–155; line H1 (patient H. P.) was started in the presence of rHBc and Mix 2. After four weeks of restimulation, the HLA class I restriction of CTL line H1 was tested by using several allogeneic target cells that were partially matched with the effector cells at the HLA class I loci but were completely HLA class II mismatched. The results, shown in FIG. 8, illustrate that the CTL activity was HLA-Aw68 restricted.

Figure 9:
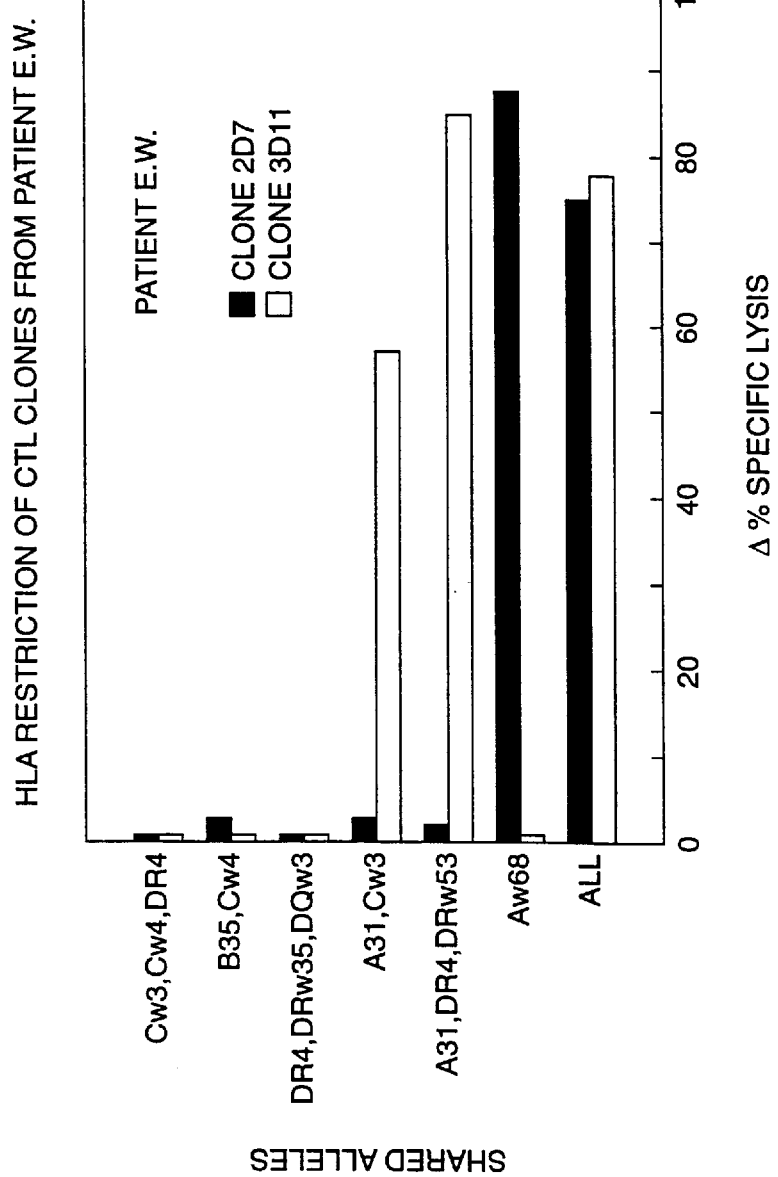
FIG. 9 shows that Aw68 and A31 are the restriction elements of the HBcAg 140–155 specific CTL response respectively of clones 2D7 and 3D1 1. Autologous and allogeneic target cells were prepulsed with peptide 140–155. Allogeneic target cells were matched at the level of class I and class II with the effector cells. The E/T ratio used was 10:1.

The HBcAg 140–155 specific CTL line E4 was cloned at 1 cell/well in the presence of anti-CD3, PHA and allogeneic PBL as feeder cells. After 2 to 3 weeks, 15% of the seeded wells showed proliferation, and the growing cell populations were tested for specific lysis of autologous B-LCL preincubated with HBcAg 140–155. Two clones (3D11, 2D7) that displayed highly efficient specific cytotoxic activity were selected for further analysis. The clones were tested against autologous and allogeneic target cells partially matched with the effectors at the level of HLA class I and class II alleles. The cytolytic activity of clone 3D11 was found to be HLA-A31 restricted and the cytolytic activity of clone 2D7, derived from the same patient, was HLA-Aw68 restricted (FIG. 9). Both clones displayed the CD4−, CD8+phenotype by flow cytometry.

These results were confirmed and extended by analysis of 4 additional HLA-A31 or Aw68 positive patients with acute HBV infection (H. F., V. T., Q. M., C. N.). In all these patients, HBcAg 140–155 specific CTL lines were generated as described for line E4 (Table III). Using partially HLA matched allogeneic target cells, the CTL response was shown to be restricted by the HLA-A31 allele in patient V. T.; it was clearly HLA-Aw68 restricted in patient Q. M. and most likely Aw68 restricted in patient C. N., whereas the response in patient H.F. was too weak to permit analysis.

TABLE III

HBCAg140–155 Specific CTL Response of CTL, Lines From HLA-A31 and Aw68 Patients with Acute HBV Infection

| Patient | HLA Match | TARGET HBCAg 140–155 | Media |
|---|---|---|---|
| | | (% Specific Lysis) | |
| V. T. | A31 | 75 | 34 |
| H. F. | ALL | 10 | 1 |
| Q. M. | Aw68 | 23 | 0 |
| C. N. | Aw68, A24 | 25 | 10 |

PBMC stimulated with HBCAg 140–155 plus rHBcAg (1μg/ml).

Figure 10A:
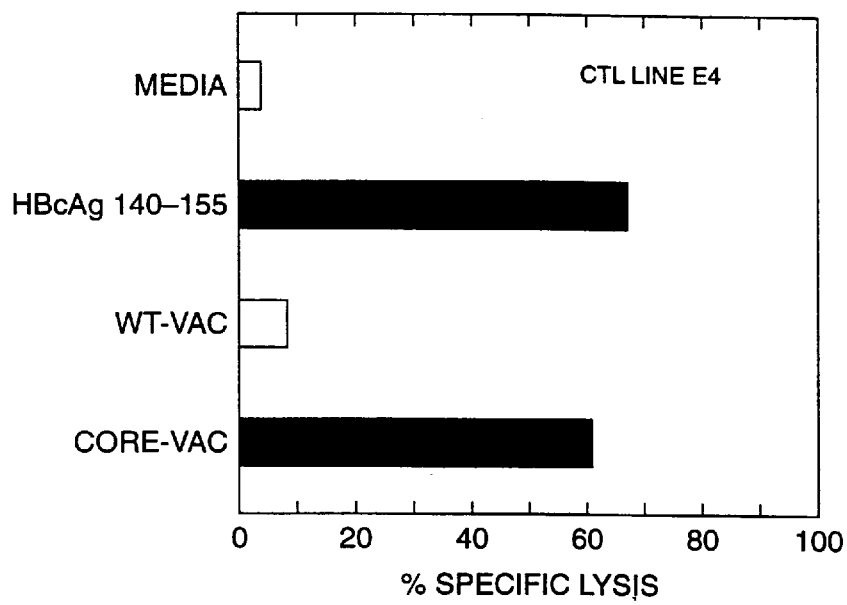
FIGS. 10A–10B illustrates that HBcAg 140–155 specific CTL lines E4 and H1 can lyse target cells expressing the endogenously synthesized antigen. The E/T ratio used for line E4 was 10:1, the E/T ratio for line H1 was 20:1 for the peptide prepulsed target cells and 15:1 for the recombinant vaccinia virus infected target cells.
Figure 10B:
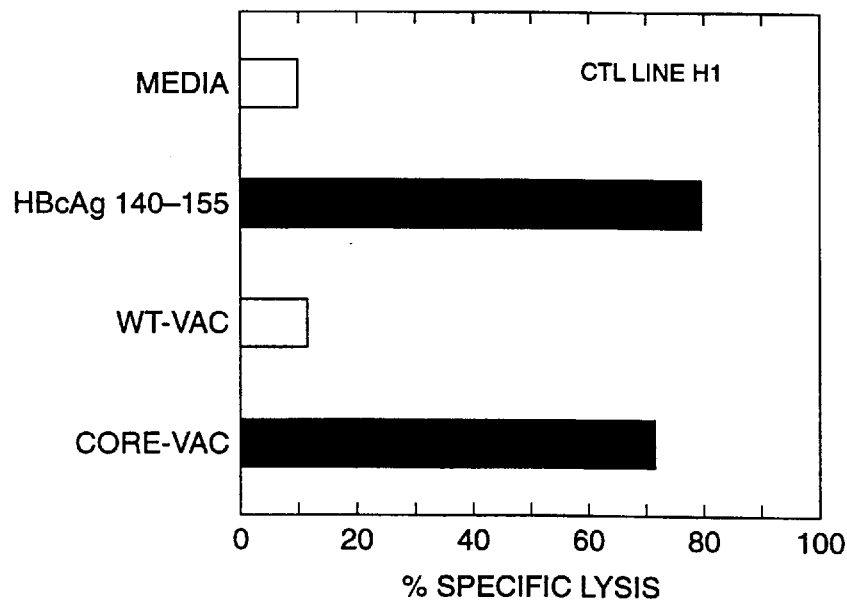

The ability of HBcAg 140–155 specific CTL lines and clones to lyse target cells that express endogenously synthesized HBcAg was determined. Two polyclonal CTL lines (E4, and H1) and two clones derived from line E4 (3D11, and 2D7) were tested for by using autologous and allogeneic target cells that had been infected with recombinant vaccinia viruses or stably transfected with the EBV based expression vectors that direct the synthesis of the HBV core and precore proteins by the cell. Line H1 was tested against endogenously synthesized core protein induced by the recombinant vaccinia virus, and line E4 was tested against endogenously synthesized core and precore proteins induced by both expression vectors (FIG. 10). Clones 3D11 and 2D7 were tested only against endogenously synthesized core and precore proteins induced by the recombinant vaccinia viruses (FIG. 11). Significant levels of specific cytolytic activity were detected in all cases (FIGS. 10 and 11). Recognition of endogenously synthesized antigen by HBcAg 140–155 peptide specific lines and clones demonstrated that the CTL epitope represented by the core sequence 140–155 is generated by the intracellular processing of endogenously synthesized HBV core and precore proteins, and that these CTL are primed in vivo during HBV infection. The latter conclusion is confirmed by the inability to establish HBcAg 140–155 specific CTL lines from 6 HLA-A31 positive or from 4 HLA-Aw68 positive normal uninfected controls.

To determine the minimum, optimally recognized HLA A31 and Aw68 restricted epitope within HBcAg 140–155, carboxy- and amino-terminal truncations of HBcAg 140–155 were produced, as shown in Table IV. Clone 3D11, which is HLA A31 restricted, and clone 2D7, which is HLA Aw68 restricted, were effector cells used to define the fine specificity of the CTL response. Autologous B-LCL were preincubated with the truncated peptides and used as targets with the two clones. The data indicate that sequence 141–151 is the minimal, optimally recognized epitope for both restriction elements. From Table IV it appears that residue 151 (Arg) defines the carboxy-terminus of the epitope recognized by both CTL clones although residue 150, which is also an arginine, can also serve as the carboxy-terminal residue, but less efficiently, for both clones as long as residue 141 serves as amino-terminus. Although residue 141 (Ser) appears to be the optimal amino-terminal residue, the data indicate that residue 142 (Thr) can also serve as the amino-terminus of the epitope for both clones if Arg 151 is the carboxy-terminal residue. In contrast, only the HLA-Aw68 restricted clone (2D7) can utilize Thr 142 if the carboxy-terminus of the peptide is extended beyond residue 151.

PMBCs were stimulated with individual peptides rather than peptide mixtures. The resulting CTL lines and/or clones were then tested for the ability to kill HLA-A2 matched target cells that were either pulsed with the peptide or that expressed the corresponding endogenous polymerase antigen (Vpol or EBO-pol). Construction of the vaccinia based

TABLE IV

FINE SPECIFICITY ANALYSIS OF CYTOTOXIC ACTIVITY OF CLONES 3D11 AND 2D7

|   |   | Clone 3D11 Restriction A31 Percent | Clone 2D7 Element Aw68 $^{51}$CrRelease |
|---|---|---|---|
| 140–155 | LSTLPETTVVRRRGRS | 72 | 62 |
| 140–154 | LSTLPETTVVRRRGR | 63 | 60 |
| 140–153 | LSTLPETTVVRRRG | 75 | 66 |
| 140–152 | LSTLPETTVVRRR | 77 | 69 |
| 140–151 | LSTLPETTVVRR | 72 | 67 |
| 140–150 | LSTLPETTVVR | 0 | 6 |
| 141–155 | STLPETTVVRRRGRS | 81 | 66 |
| 141–154 | STLPETTVVRRRGR | 79 | 67 |
| 141–153 | STLPETTVVRRRG | 79 | 59 |
| 141–152 | STLPETTVVRRR | 68 | 68 |
| 141–151 | STLPETTVVRR | 69 | 66 |
| 141–150 | STLPETTVVR | 20 | 52 |
| 141–149 | STLPETTVV | 0 | 3 |
| 142–155 | TLPETTVVRRRGRS | 8 | 63 |
| 142–154 | TLPETTVVRRRGR | 18 | 54 |
| 142–153 | TLPETTVVRRRG | 8 | 56 |
| 142–152 | TLPETTVVRRR | 2 | 37 |
| 142–151 | TLPETTVVRR | 47 | 60 |
| 142–150 | TLPETTVVR | 0 | 0 |
| 143–155 | LPETTVVRRRGRS | 0 | 0 |
| 143–154 | LPETTVVRRRGR | 0 | 0 |
| 143–153 | LPETTVVRRRG | 0 | 0 |
| 143–152 | LPETTVVRRR | 0 | 2 |
| 143–151 | LPETTVVRR | 0 | 0 |

Figure 12A:
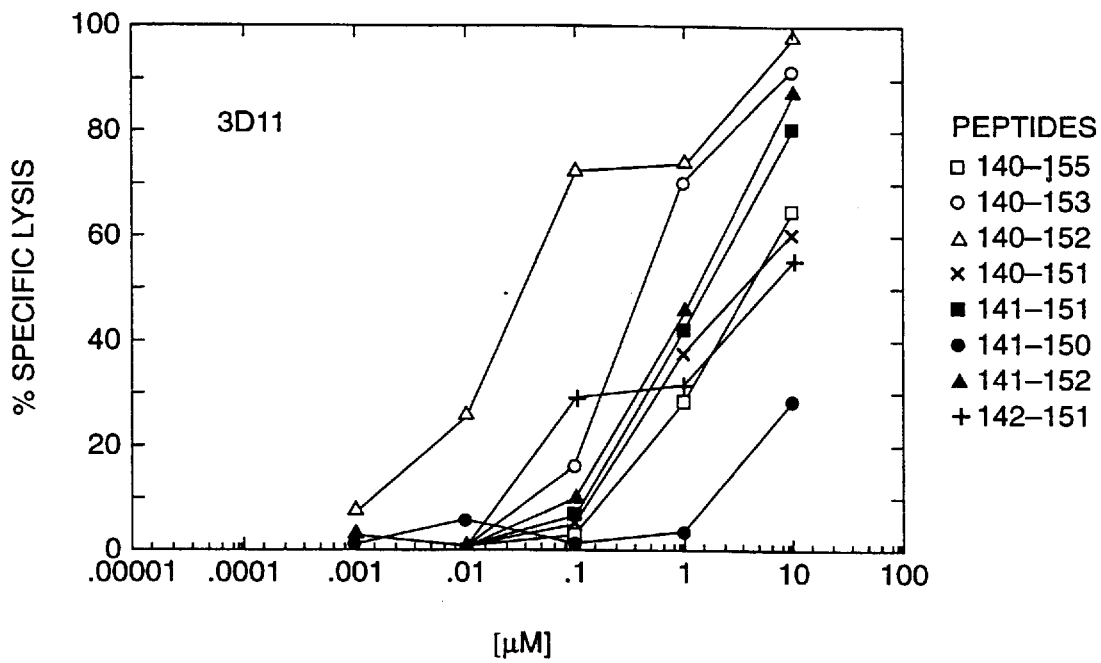
FIGS. 12A–12B illustrates the results of experiments that show peptide 141–151 is the shortest optimally recognized sequence in HBcAg 140–155 for both of the restriction elements. Clone 3D11 was tested against allogeneic A31-positive target cells and clone 2D7 against allogeneic Aw68-positive target cells. Target cells were prepulsed with peptide concentration ranging between 0.001 to 1 $\mu$M. The E/T ratio used was 10:1.
Figure 12B:
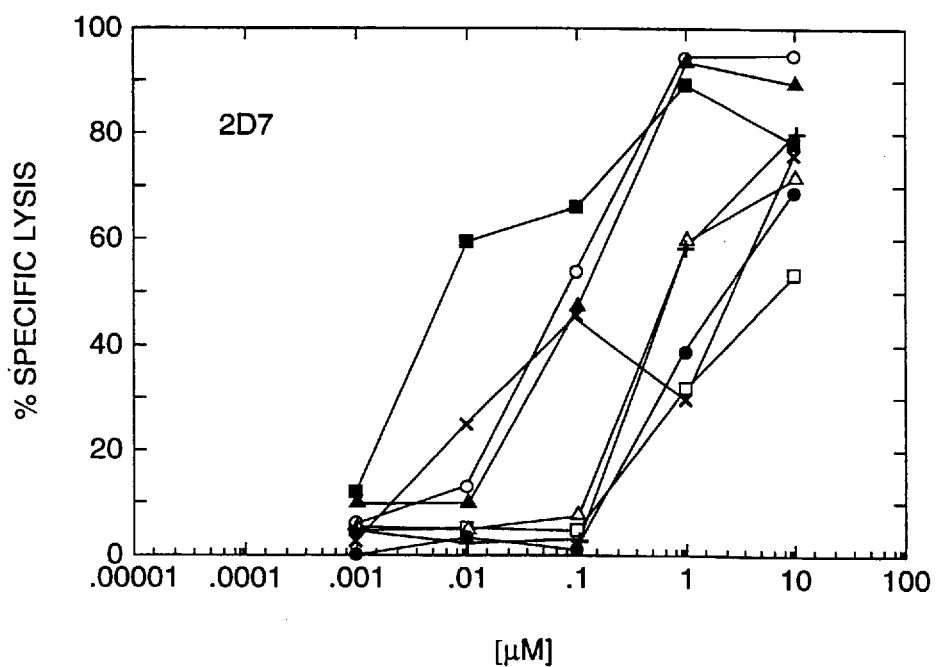

To more precisely define the boundaries of the epitope(s), a dose titration analysis was conducted in which the two CTL clones were incubated with allogeneic HLA-A31 and HLA-Aw68 positive target cells preincubated with peptides 140–151, 141–150, 141–151, 141–152, 142–151 at different molar concentrations ranging from $10^{-3}$ μM to 1 μM. As shown in FIG. 12, residues 141–151 represent a minimal optimally recognized epitope recognized by both of the CTL clones. Amino-terminal elongation by one residue did not affect efficiency of target lysis by either clone, while the addition of one amino acid at the carboxy terminus reduced the CTL response ten-fold for both HLA A31 and Aw68 restricted clones, demonstrating that both HLA alleles bind and present the same peptide to their corresponding CTL.

EXAMPLE VII

HLA-Restricted CTL Response TO HBV Polymerase Epitopes

This Example describes the identification of an HLA-A2 restricted CTL response to two HBV polymerase peptides in a patient with acute viral hepatitis. The epitopes are present in amino acid sequences HBpol$_{61-69}$ (Seq. ID No. 9]Gly-Leu-Tyr-Ser-Ser-Thr-Val-Pro-Val (GLYSSTVPV) (also designated peptide 927.32 in the Figures) and HBpol$_{803-811}$ [Seq. ID No. 10]Ser-Leu -Tyr-Ala-Asp-Ser-Pro-Ser-Val (SLYADSPSV) (also designated peptide 927.27 in the Figures.).

The CTL induced by the HBpol peptides were identified in PBMCs from a patient with acute hepatitis according to the procedure set forth in Example VI, except that the Vpol and Epstein-Barr virus based EBO-pol constructs was as described in Example II.

Figure 13:
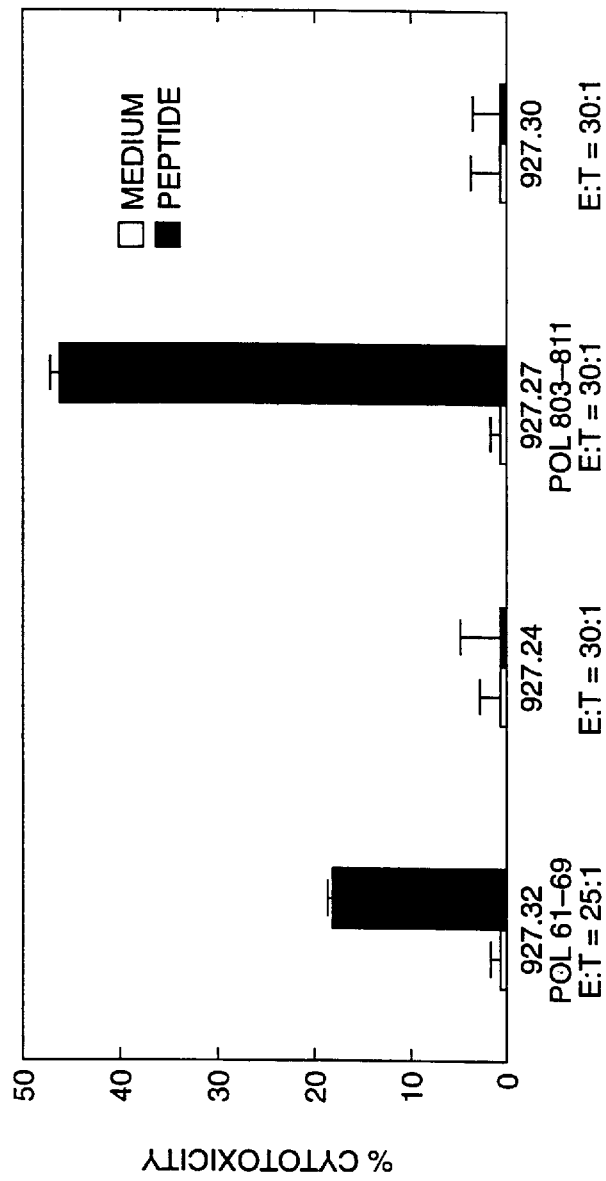
FIG. 13 shows the CTL response to two polymerase peptides that contain the HLA-A2 motif in a patient using target cells pulsed with peptide that match only at HLA-A2.
Figure 14:
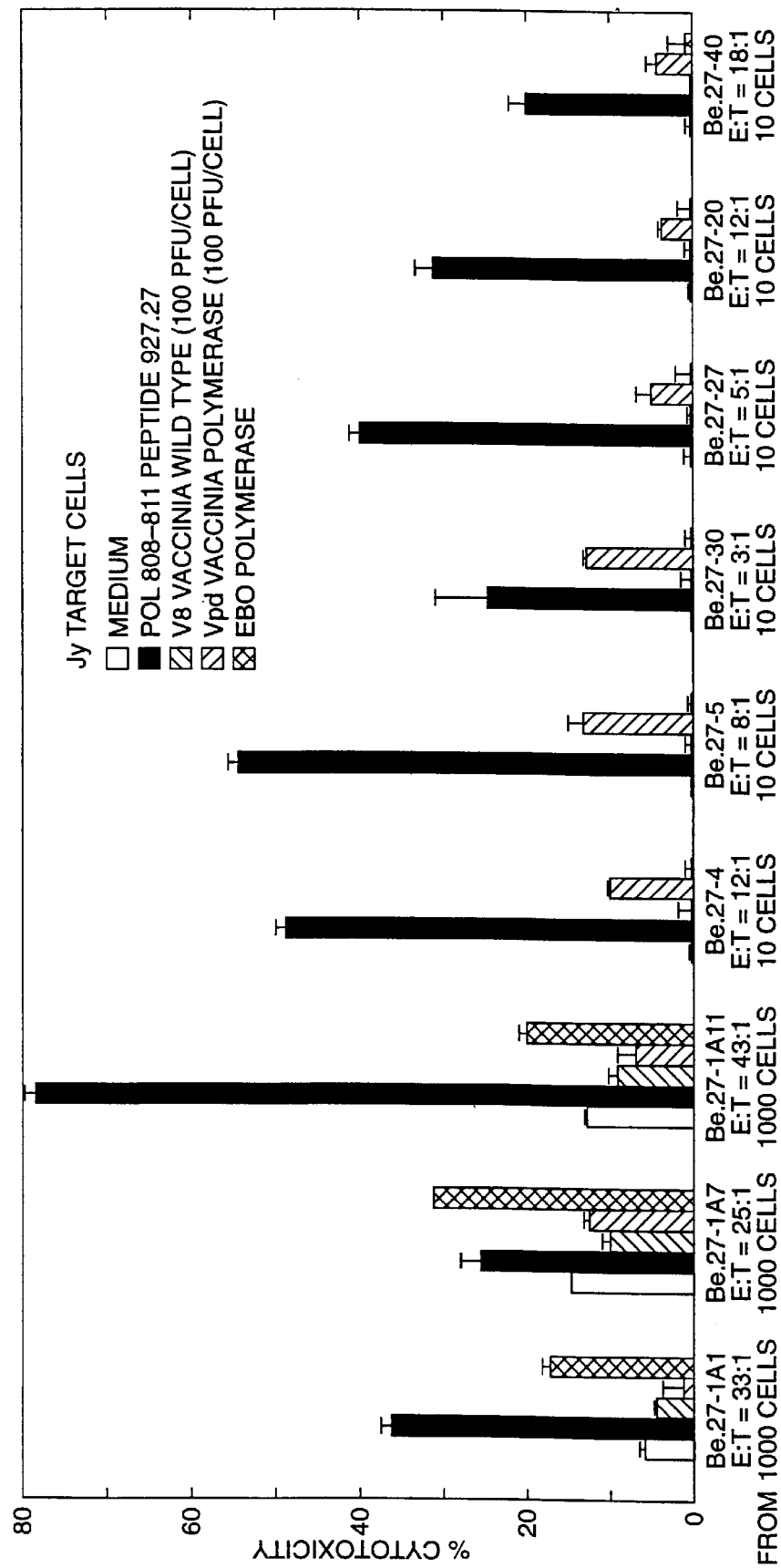
FIG. 14 shows the ability of several polymerase 803–811 peptide specific clones to recognize endogenously synthesized polymerase.
Figure 15A:
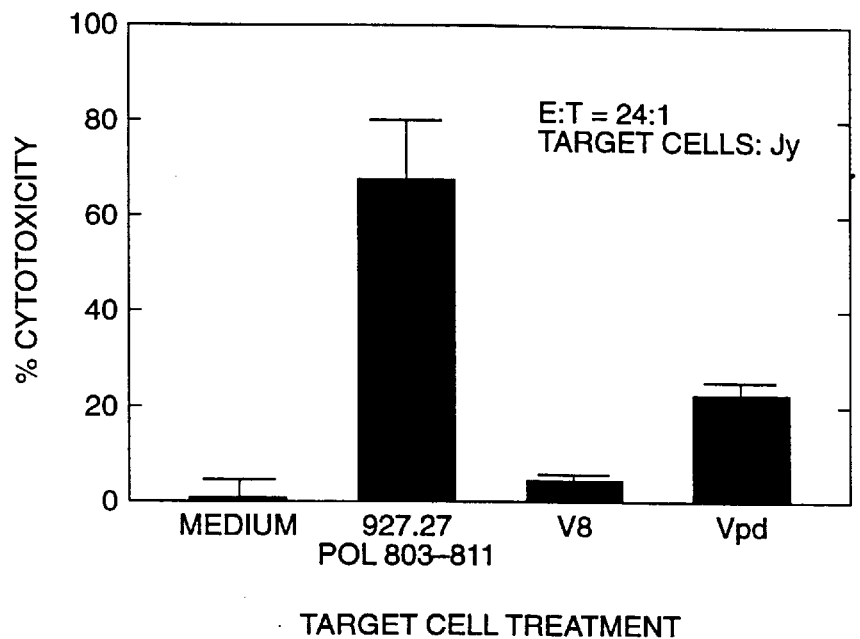
FIGS. 15A–15B shows that the CTL response to polymerase peptide 803–811 can recognize cells pulsed with peptide and endogenously synthesized polymerase (Vpol), whereas the CTL response to polymerase peptide 61–69 only recognized cells pulsed with the 61–69 peptide.
Figure 15B:
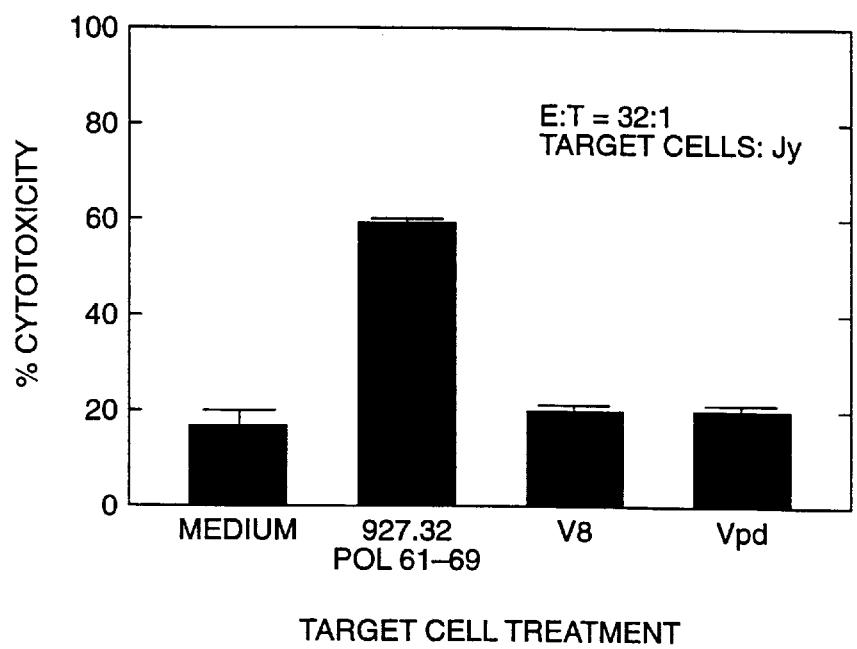

As shown in FIG. 13, both peptides HBpol$_{803-811}$ and HBpol$_{61-69}$ stimulated CTL responses in a patient (HLA-A2$^+$) using target cells pulsed with peptide, whereas other peptides 927.24 (WILRGTSFR) and 927.30 (DLNLGNLNV) and media controls did not stimulate the specific CTL response. The ability of the HBpol$_{803-811}$ specific clones to recognize endogenously synthesized polymerase antigen (Vpol and EBO-pol) is shown in FIG. 14. Two clones, designated Be.27-1A1 and Be.27-A1A5, were identified that recognized the HBpol$_{803-811}$ peptide. As shown in FIG. 15, CTL responses to HBpol$_{61-69}$ and HBpol$_{803-811}$ were shown with target cells pulsed with homologous peptide, but only the HBpol$_{803-811}$ clone showed a response to endogenously synthesized Vpol antigen.

EXAMPLE VIII

HLA-Restricted CTL Response TO HBV X Protein

This Example describes the identification of an HLA-A2 restricted CTL response in a patient with acute viral hepatitis to a peptide sequence derived from the HBV X protein. The CTL epitope is present in a peptide of the amino acid sequence HBx$_{126-134}$ [Seq. ID No. 3]Glu-Ile-Arg-Leu-Lys-Val-Phe-Val-Leu (EIRLKVFVL).

The CTL induced by the HBpol peptides were identified in PBMCs from a patient with acute hepatitis according to the procedure set forth in Example VI, except that the PMBCs were stimulated with individual peptides rather than peptide mixtures. The resulting CTL lines were then tested for the ability to kill HLA-A2 matched target cells that were pulsed with the peptide.

Figure 16:
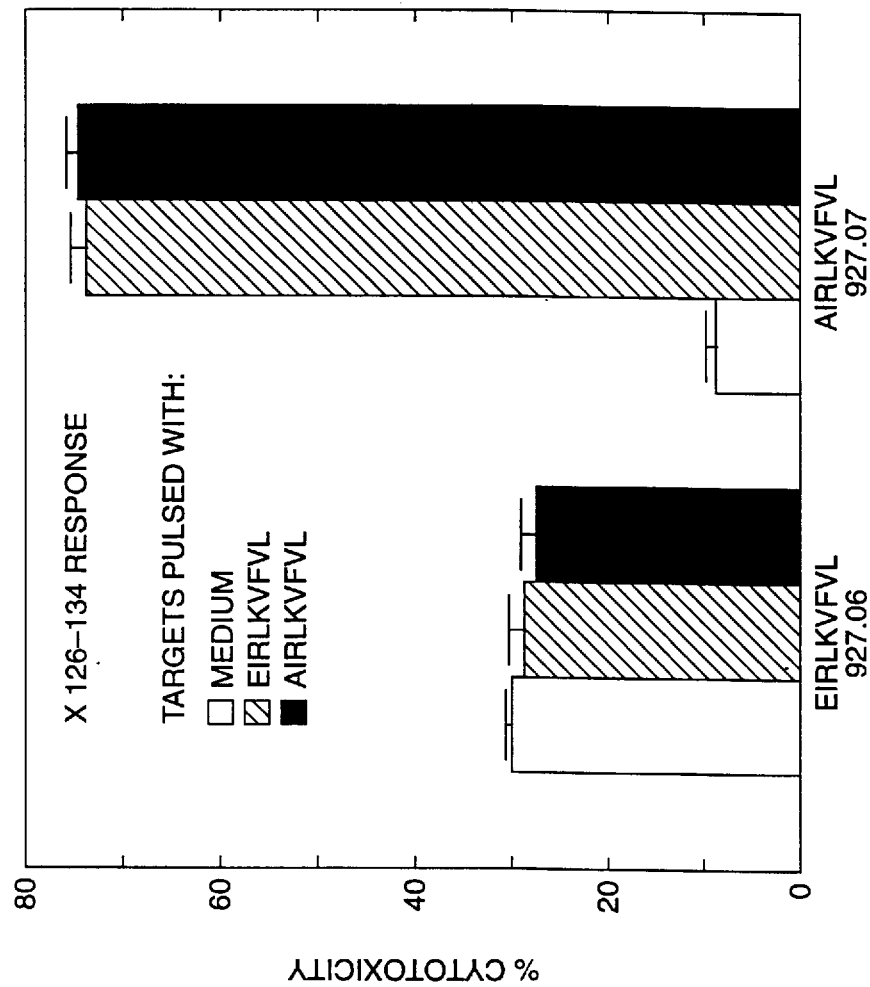
FIG. 16 shows the induction of a CTL response by a HBX 126–134 peptide analog but not by the wild type.

As shown in FIG. 16, CTL were stimulated by HBx peptide 126–134 where the amino terminal residue had been substituted with an alanine residue (EIRLKVFVL→AIRLKVFVL). CTL that recognized the analog peptide also recognized the peptide with the wild type sequence. On the other hand, the wild type peptide was not able to induce a specific CTL response detectable with cells pulsed with either peptide.

EXAMPLE IX

HLA-Restricted CTL Response to HBenv348–357

This Example describes the identification of an HLA-A2 restricted CTL response in a patient with acute viral hepatitis to a peptide sequence derived from the HBV envelope protein. The CTL epitope is present in a peptide of the amino acid sequence HBenv$_{348-357}$ [Seq. ID No. 11]Gly-Leu-Ser-Pro-Thr-Val-Trp-Leu-Ser-Val (subtype ayw) (Ala is substituted for the C-terminal Val in subtype adw).

The CTL induced by the HBenv 348–357 peptide were identified in PBMCs from a patient with acute hepatitis according to the procedure set forth in Example VI, except that the PMBCs were stimulated with individual peptide rather than peptide mixtures. The resulting CTL line was then tested for the ability to kill HLA-A2 matched target cells that were pulsed with the peptide or that expressed endogenous envelope antigens of ayw or adw subtypes.

Figure 17:
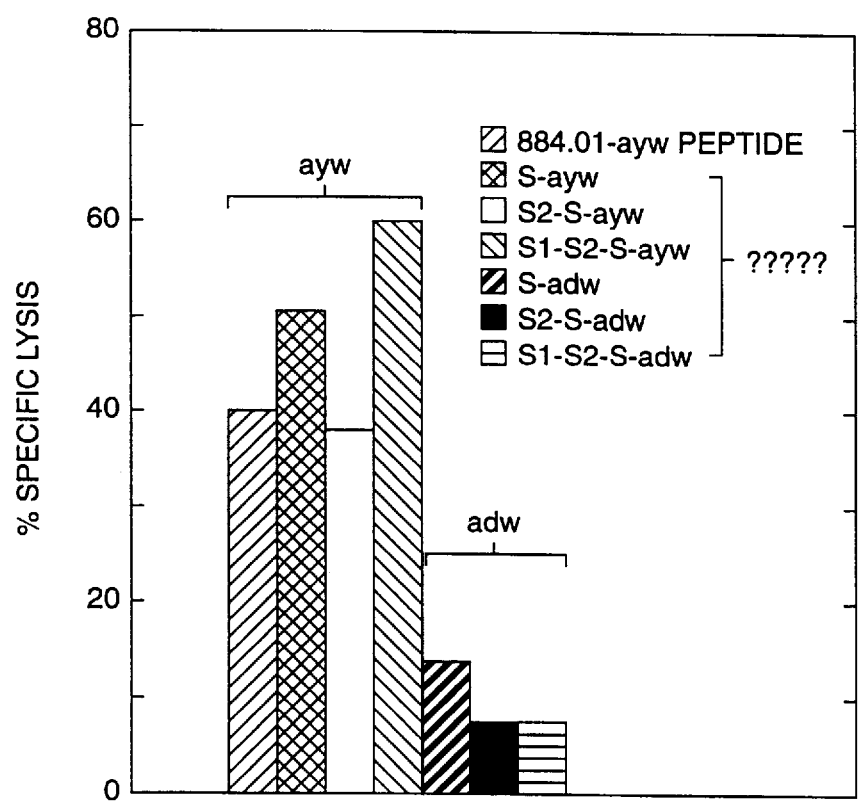
FIG. 17 shows the CTL response stimulated by HBenv peptide 348–357 to target cells pulsed with homologous peptide (designated 884.01-ayw) and to endogenous envelope antigen of the ayw subtype, but the lack of response to cells expressing antigen of the adw subtype.

As shown in FIG. 17, CTL stimulated by HBenv peptide 348–357 responded to target cells (at effector:target cell ratio of 3:1) pulsed with peptide (designated 884.01-ayw) and to endogenous envelope antigen of the ayw subtype, but did not recognize the adw subtype, presumably due to the difference in the carboxyterminal amino acid residue (Ala substituted for Val).

The results described in the foregoing Examples illustrate that the CTL response to HBV in man appears to be quite polyvalent, presumably to afford efficient protection from this serious viral infection. Furthermore the data indicate that the peptide stimulation strategy employed herein is both efficient and effective for the identification and analysis of the polyvalent response, restricted as it is by the polymorphic HLA class I locus. As additional HLA allele specific binding motifs are identified, HBV-derived peptides containing these motifs can be used for in vitro stimulation of CTL precursors.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A peptide containing at least one cytotoxic T lymphocyte (CTL) epitope, the peptide comprising from eight to seventeen amino acids and including at least seven contiguous amino acids of a corresponding portion of $HBpol_{803-811}$ having the following sequence:

VIII ($HBpol_{803-811}$) (Seq. ID No. 10) Ser-Leu-Tyr-Ala-Asp-Ser-Pro-Ser-Val.

2. The peptide of claim 1, which is

VIII ($HBpol_{803-811}$) [Seq. ID No. 10]Ser-Leu-Tyr-Ala-Asp-Ser-Pro-Ser-Val.

3. An immunogenic polypeptide composition comprising the peptide of claim 1 joined to and a second immunogenic peptide to form a heteropolymer.

4. The immunogenic polypeptide composition of claim 3, wherein the second immunogenic peptide elicits a immune response specific for hepatitis B virus.

5. The immunogenic polypeptide composition of claim 4, wherein the second immunogenic peptide elicits a T-helper cell mediated response.

6. An immunogenic conjugate composition comprising the peptide of claim 1 conjugated to a immunogenic lipid carrier.

7. The immunogenic conjugate composition of claim 6, wherein the lipid carrier enhances a human T-lymphocyte response.

8. The immunogenic conjugate composition of claim 7, wherein the lipid carrier is a lipopeptide.

9. A peptide according to claim 1 which is expressed by a DNA construct that comprises a transcriptional promotor, a DNA sequence encoding said peptide, and a transcription terminator, each operably linked for expression of said peptide.

10. The peptide according to claim 1 comprising from eight to twelve amino acid residues.

11. The peptide according to claim 10 comprising nine or ten amino acid residues.

12. The peptide according to claim 11, which is ($HBpol_{803-811}$) [Seq. ID No. 10]Ser-Leu-Tyr-Ala-Asp-Ser-Pro-Ser-Val.

* * * * *

UNITED STATES PATENT AND TRADEMARK OFFICE
CERTIFICATE OF CORRECTION

PATENT NO.   : 5,840,303
DATED        : November 24, 1998
INVENTOR(S)  : Francis V. Chisari, Carlo Ferrari, Amalia Penna and Gabriele Missale It is certified that error appears in the above-identified patent and that said Letters Patent is hereby corrected as shown below:

Column 1,
Line 12, please delete the present paragraph and insert therefor:
-- GOVERNMENT SUPPORT
This invention was made with government support under Contract Nos. AI 20001 by the National Institutes of Health. The government has certain rights in this invention. --

Signed and Sealed this

Twenty-eighth Day of May, 2002

Attest:

JAMES E. ROGAN
Attesting Officer    Director of the United States Patent and Trademark Office

UNITED STATES PATENT AND TRADEMARK OFFICE
CERTIFICATE OF CORRECTION

PATENT NO. : 5,840,303
DATED : November 24, 1998
INVENTOR(S) : Francis V. Chisari et al.

It is certified that error appears in the above-identified patent and that said Letters Patent is hereby corrected as shown below:

<u>Title page,</u>
Item [73], Assignee, "The Scripps Research Foundation" should read -- The Scripps Research Institute --.

Signed and Sealed this

Twenty-third Day of May, 2006

JON W. DUDAS
*Director of the United States Patent and Trademark Office*

UNITED STATES PATENT AND TRADEMARK OFFICE
Certificate

Patent No. 5,840,303                                                      Patented: November 23, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Francis V. Chisari, Del Mar, CA (US).

Signed and Sealed this Twenty-fifth Day of September 2007.

WILLIAM R. DIXON, JR.
*Special Program Examiner*
Technology Center 1600

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Ser  Thr  Leu  Pro  Glu  Thr  Thr  Val  Val  Arg  Arg
    1                        5                                  10

( 2 ) INFORMATION FOR SEQ ID NO:2:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Ala  Thr  Val  Glu  Leu  Leu  Ser  Phe  Leu  Pro  Ser  Asp  Phe  Phe  Pro  Ser
    1                        5                                10                              15

Val ( 2 ) INFORMATION FOR SEQ ID NO:3:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:3:

Glu Ile Arg Leu Lys Val Phe Val Leu
1               5

( 2 ) INFORMATION FOR SEQ ID NO:4:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:4:

Leu Pro Ser Asp Phe Phe Pro Ser Val
1               5

( 2 ) INFORMATION FOR SEQ ID NO:5:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:5:

Phe Leu Pro Ser Asp Phe Phe Pro Ser Val
1               5                   10

( 2 ) INFORMATION FOR SEQ ID NO:6:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:6:

Gly Arg Glu Thr Val Ile Glu Tyr Leu Val Ser Phe Gly Val Trp
1               5                   10                  15

( 2 ) INFORMATION FOR SEQ ID NO:7:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:7:

Leu Ser Thr Leu Pro Glu Thr Thr Val Val Arg Arg Arg Gly Arg
1               5                   10                  15

( 2 ) INFORMATION FOR SEQ ID NO:8:

( i ) SEQUENCE CHARACTERISTICS:
　　　　( A ) LENGTH: 20 amino acids
　　　　( B ) TYPE: amino acid
　　　　( C ) STRANDEDNESS: single
　　　　( D ) TOPOLOGY: linear ( i i ) MOLECULE TYPE: peptide ( x i ) SEQUENCE DESCRIPTION: SEQ ID NO:8:

Arg Asp Leu Leu Asp Thr Ala Ser Ala Leu Tyr Arg Glu Ala Leu Glu
1               5                   10                  15

Ser Pro Glu His
            20

( 2 ) INFORMATION FOR SEQ ID NO:9:

( i ) SEQUENCE CHARACTERISTICS:
　　　　( A ) LENGTH: 9 amino acids
　　　　( B ) TYPE: amino acid
　　　　( C ) STRANDEDNESS: single
　　　　( D ) TOPOLOGY: linear ( i i ) MOLECULE TYPE: peptide ( x i ) SEQUENCE DESCRIPTION: SEQ ID NO:9:

Gly Leu Tyr Ser Ser Thr Val Pro Val
1               5

( 2 ) INFORMATION FOR SEQ ID NO:10:

( i ) SEQUENCE CHARACTERISTICS:
　　　　( A ) LENGTH: 9 amino acids
　　　　( B ) TYPE: amino acid
　　　　( C ) STRANDEDNESS: single
　　　　( D ) TOPOLOGY: linear ( i i ) MOLECULE TYPE: peptide ( x i ) SEQUENCE DESCRIPTION: SEQ ID NO:10:

Ser Leu Tyr Ala Asp Ser Pro Ser Val
1               5

( 2 ) INFORMATION FOR SEQ ID NO:11:

( i ) SEQUENCE CHARACTERISTICS:
　　　　( A ) LENGTH: 10 amino acids
　　　　( B ) TYPE: amino acid
　　　　( C ) STRANDEDNESS: single
　　　　( D ) TOPOLOGY: linear ( i i ) MOLECULE TYPE: peptide ( x i ) SEQUENCE DESCRIPTION: SEQ ID NO:11:

Gly Leu Ser Pro Thr Val Trp Leu Ser Val
1               5                   10

( 2 ) INFORMATION FOR SEQ ID NO:12:

( i ) SEQUENCE CHARACTERISTICS:
　　　　( A ) LENGTH: 16 amino acids
　　　　( B ) TYPE: amino acid
　　　　( C ) STRANDEDNESS: single
　　　　( D ) TOPOLOGY: linear ( i i ) MOLECULE TYPE: peptide ( x i ) SEQUENCE DESCRIPTION: SEQ ID NO:12:

Leu Ser Thr Leu Pro Glu Thr Thr Val Val Arg Arg Arg Gly Arg Ser
1               5                   10                  15

( 2 ) INFORMATION FOR SEQ ID NO:13:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Leu Ser Thr Leu Pro Glu Thr Thr Val Val Arg Arg Arg Gly
1               5                   10
```

( 2 ) INFORMATION FOR SEQ ID NO:14:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Leu Ser Thr Leu Pro Glu Thr Thr Val Val Arg Arg Arg
1               5                   10
```

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Leu Ser Thr Leu Pro Glu Thr Thr Val Val Arg Arg
1               5                   10
```

( 2 ) INFORMATION FOR SEQ ID NO:16:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Leu Ser Thr Leu Pro Glu Thr Thr Val Val Arg
1               5                   10
```

( 2 ) INFORMATION FOR SEQ ID NO:17:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Ser Thr Leu Pro Glu Thr Thr Val Val Arg Arg Arg Gly Arg Ser
1               5                   10                  15
```

( 2 ) INFORMATION FOR SEQ ID NO:18:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Ser  Thr  Leu  Pro  Glu  Thr  Thr  Val  Val  Arg  Arg  Arg  Gly  Arg
1                  5                             10
```

( 2 ) INFORMATION FOR SEQ ID NO:19:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Ser  Thr  Leu  Pro  Glu  Thr  Thr  Val  Val  Arg  Arg  Arg  Gly
1                  5                             10
```

( 2 ) INFORMATION FOR SEQ ID NO:20:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

```
Ser  Thr  Leu  Pro  Glu  Thr  Thr  Val  Val  Arg  Arg  Arg
1                  5                             10
```

( 2 ) INFORMATION FOR SEQ ID NO:21:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

```
Ser  Thr  Leu  Pro  Glu  Thr  Thr  Val  Val  Arg
1                  5                             10
```

( 2 ) INFORMATION FOR SEQ ID NO:22:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Ser  Thr  Leu  Pro  Glu  Thr  Thr  Val  Val
1                  5
```

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Thr Leu Pro Glu Thr Thr Val Val Arg Arg Arg Gly Arg Ser
1               5                   10
```

(2) INFORMATION FOR SEQ ID NO:24:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Thr Leu Pro Glu Thr Thr Val Val Arg Arg Arg Gly Arg
1               5                   10
```

(2) INFORMATION FOR SEQ ID NO:25:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Thr Leu Pro Glu Thr Thr Val Val Arg Arg Arg Gly
1               5                   10
```

(2) INFORMATION FOR SEQ ID NO:26:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Thr Leu Pro Glu Thr Thr Val Val Arg Arg Arg
1               5                   10
```

(2) INFORMATION FOR SEQ ID NO:27:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Thr Leu Pro Glu Thr Thr Val Val Arg Arg
1               5                   10
```

( 2 ) INFORMATION FOR SEQ ID NO:28:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

```
Thr Leu Pro Glu Thr Thr Val Val Arg
1               5
```

( 2 ) INFORMATION FOR SEQ ID NO:29:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

```
Leu Pro Glu Thr Thr Val Val Arg Arg Arg Gly Arg Ser
1               5                   10
```

( 2 ) INFORMATION FOR SEQ ID NO:30:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

```
Leu Pro Glu Thr Thr Val Val Arg Arg Arg Gly Arg
1               5                   10
```

( 2 ) INFORMATION FOR SEQ ID NO:31:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

```
Leu Pro Glu Thr Thr Val Val Arg Arg Arg Gly
1               5                   10
```

( 2 ) INFORMATION FOR SEQ ID NO:32:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

```
Leu Pro Glu Thr Thr Val Val Arg Arg Arg
1               5                   10
```

( 2 ) INFORMATION FOR SEQ ID NO:33:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:33:

```
Leu  Pro  Glu  Thr  Thr  Val  Val  Arg  Arg
1                   5
```

( 2 ) INFORMATION FOR SEQ ID NO:34:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:34:

```
Met  Asp  Ile  Asp  Pro  Tyr  Lys  Glu  Phe  Gly  Ala  Thr  Val  Glu  Leu  Leu
1                   5                             10                            15
Ser  Phe  Leu  Pro
               20
```

( 2 ) INFORMATION FOR SEQ ID NO:35:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:35:

```
Pro  His  His  Tyr  Ala  Leu  Arg  Gln  Ala  Ile  Leu  Cys  Trp  Gly  Glu  Leu
1                   5                             10                            15
Met  Tyr  Leu  Ala
               20
```

( 2 ) INFORMATION FOR SEQ ID NO:36:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:36:

```
Leu  Leu  Trp  Phe  His  Ile  Ser  Cys  Leu  Thr  Phe  Gly  Arg  Glu  Thr  Val
1                   5                             10                            15
Ile  Glu  Tyr  Leu
               20
```

( 2 ) INFORMATION FOR SEQ ID NO:37:

( i ) SEQUENCE CHARACTERISTICS:
    ( A ) LENGTH: 15 amino acids
    ( B ) TYPE: amino acid
    ( C ) STRANDEDNESS: single

```
            ( D ) TOPOLOGY: linear ( i i ) MOLECULE TYPE: peptide ( x i ) SEQUENCE DESCRIPTION: SEQ ID NO:37:

Glu  Tyr  Leu  Val  Ser  Phe  Gly  Val  Trp  Ile  Arg  Thr  Pro  Pro  Ala
    1                   5                        10                       15

( 2 ) INFORMATION FOR SEQ ID NO:38:

( i ) SEQUENCE CHARACTERISTICS:
            ( A ) LENGTH: 20 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:38:

Val  Ser  Phe  Gly  Val  Trp  Ile  Arg  Thr  Pro  Pro  Ala  Tyr  Arg  Pro  Pro
    1                   5                        10                       15

Asn  Ala  Pro  Ile
                    20
```